(12) United States Patent
Krisko et al.

(10) Patent No.: US 6,939,446 B2
(45) Date of Patent: Sep. 6, 2005

(54) SOIL-RESISTANT COATING FOR GLASS SURFACES

(75) Inventors: Annette J. Krisko, Prairie de Sac, WI (US); Klaus Hartig, Avcoa, WI (US); Roger D. O'Shaughnessy, Eden Prairie, MN (US)

(73) Assignee: Cardinal CG Company, Minnetonka, MN (US)

( * ) Notice: Subject to any disclaimer, the term of this patent is extended or adjusted under 35 U.S.C. 154(b) by 0 days.

(21) Appl. No.: 10/464,528

(22) Filed: Jun. 17, 2003

(65) Prior Publication Data

US 2003/0228431 A1 Dec. 11, 2003

Related U.S. Application Data

(63) Continuation of application No. 09/599,301, filed on Jun. 21, 2000, now Pat. No. 6,660,365, which is a continuation-in-part of application No. PCT/US99/02208, filed on Feb. 2, 1999.

(60) Provisional application No. 60/168,497, filed on Dec. 2, 1999, and provisional application No. 60/113,259, filed on Dec. 21, 1998.

(51) Int. Cl.[7] .............................................. C23C 14/35
(52) U.S. Cl. ............................. 204/192.23; 204/192.26
(58) Field of Search ....................... 204/192.12, 192.15, 204/192.23, 192.26

(56) References Cited

U.S. PATENT DOCUMENTS

| | | | |
|---|---|---|---|
| 2,780,553 A | 2/1957 | Pawlyk | 106/1 |
| 2,808,351 A | 10/1957 | Colbert et al. | 117/211 |
| 3,505,092 A | 4/1970 | Ryan et al. | 117/33.3 |
| 3,528,906 A | 9/1970 | Cash, Jr. et al. | 204/298 |
| 3,840,451 A | 10/1974 | Golyanov et al. | 204/192 |
| 3,844,924 A | 10/1974 | Cunningham et al. | 204/298 |
| 3,852,098 A | 12/1974 | Bloss et al. | 117/106 R |
| 3,925,182 A | 12/1975 | Carmichael et al. | 204/192 |
| 3,968,018 A | 7/1976 | Lane et al. | 204/192 |
| 3,970,037 A | 7/1976 | Sopko | 118/48 |
| 3,990,784 A | 11/1976 | Gelber | 350/166 |
| 4,045,125 A | 8/1977 | Farges | 350/166 |
| 4,052,520 A | 10/1977 | Chang et al. | 427/164 |

(Continued)

FOREIGN PATENT DOCUMENTS

| | | | |
|---|---|---|---|
| EP | 0 637 572 A1 | 2/1995 | C03C/17/34 |
| EP | 0 689 962 B1 | 1/1996 | B60B/1/06 |
| EP | 0 689 962 A2 | 1/1996 | B60B/1/06 |
| EP | 0 820 967 A1 | 1/1998 | C03C/17/34 |
| WO | WO 92/17621 | 10/1992 | C23C/14/34 |

*Primary Examiner*—Steven VerSteeg
(74) *Attorney, Agent, or Firm*—Fredrikson & Byron, P.A.

(57) ABSTRACT

A glass article which has a water-sheeting coating and a method of applying coatings to opposed sides of a substrate are described. In one embodiment, a water-sheeting coating 20 comprising silica is sputtered directly onto an exterior surface of the glass. The exterior face of this water-sheeting coating is substantially non-porous but has an irregular surface. This water-sheeting coating causes water applied to the coated surface to sheet, making the glass article easier to clean and helping the glass stay clean longer. In one method of the invention, interior and exterior surfaces of a glass sheet are cleaned. Thereafter, the interior surface of the sheet of glass is coated with a reflective coating by sputtering, in sequence, at least one dielectric layer, at least one metal layer, and at least one dielectric layer. The exterior surface of the glass is coated with a water-sheeting coating by sputtering silica directly onto the exterior surface of the sheet of glass. If so desired, both the interior surface and the exterior surface can be applied during the same pass through the same sputter coating apparatus while the glass maintains a constant orientation wherein the interior surface is positioned above the exterior surface.

18 Claims, 10 Drawing Sheets

U.S. PATENT DOCUMENTS

| | | | |
|---|---|---|---|
| 4,060,660 A | 11/1977 | Carlson et al. | 428/408 |
| 4,107,350 A | 8/1978 | Berg et al. | 427/38 |
| 4,130,672 A | 12/1978 | Onoki et al. | 427/164 |
| 4,166,018 A | 8/1979 | Chapin | 204/192 R |
| 4,194,022 A | 3/1980 | Gillery | 427/109 |
| 4,212,663 A | 7/1980 | Aslami | 65/144 |
| 4,212,903 A | 7/1980 | Schnell et al. | 427/127 |
| 4,214,014 A | 7/1980 | Hofer et al. | 427/40 |
| 4,261,722 A | 4/1981 | Novak et al. | 65/600 |
| 4,332,922 A | 6/1982 | Kossmehl et al. | 525/478 |
| 4,351,861 A | 9/1982 | Henery | 427/255.1 |
| 4,377,613 A | 3/1983 | Gordon | 428/212 |
| 4,466,258 A | 8/1984 | Sando et al. | 68/5 C |
| 4,485,146 A | 11/1984 | Mizuhashi et al. | 428/428 |
| 4,486,286 A | 12/1984 | Lewin et al. | 204/192 C |
| 4,503,125 A | 3/1985 | Nelson et al. | 428/408 |
| 4,504,519 A | 3/1985 | Zelez | 427/39 |
| 4,568,622 A | 2/1986 | Minami et al. | 430/57 |
| 4,569,738 A | 2/1986 | Kieser et al. | 204/173 |
| 4,571,350 A | 2/1986 | Parker et al. | 427/109 |
| 4,661,409 A | 4/1987 | Kieser et al. | 428/408 |
| 4,704,339 A | 11/1987 | Green et al. | 428/689 |
| 4,713,311 A | 12/1987 | Senske et al. | 430/127 |
| 4,717,622 A | 1/1988 | Kurokawa et al. | 428/408 |
| 4,725,345 A | 2/1988 | Sakamoto et al. | 204/192.31 |
| 4,728,529 A | 3/1988 | Etzkorn et al. | 427/39 |
| 4,732,454 A | 3/1988 | Saito et al. | 350/164 |
| 4,737,252 A | 4/1988 | Hoffman | 204/192.16 |
| 4,769,291 A | 9/1988 | Belkind et al. | 428/630 |
| 4,777,090 A | 10/1988 | Ovshinsky et al. | 428/408 |
| 4,780,334 A | 10/1988 | Ackerman | 427/248.1 |
| 4,816,127 A | 3/1989 | Eltoukhy | 204/192.15 |
| 4,849,081 A | 7/1989 | Ross | 204/192.15 |
| 4,851,095 A | 7/1989 | Scobey et al. | 204/192.12 |
| 4,859,493 A | 8/1989 | Lemelson | 427/45.1 |
| 4,882,827 A | 11/1989 | Kusumi et al. | 29/527.2 |
| 4,894,133 A | 1/1990 | Hedgcoth | 204/192.15 |
| 4,915,977 A | 4/1990 | Okamoto et al. | 427/37 |
| 4,919,778 A | 4/1990 | Dietrich et al. | 204/192.27 |
| 4,961,958 A | 10/1990 | Desphandey et al. | 427/38 |
| 4,981,568 A | 1/1991 | Taranko et al. | 204/192.31 |
| 5,008,002 A | 4/1991 | Uno et al. | 204/192.31 |
| 5,026,415 A | 6/1991 | Yamamoto et al. | 65/305 |
| 5,032,421 A | 7/1991 | Sarma et al. | 427/38 |
| 5,047,131 A | 9/1991 | Wolfe et al. | 204/192.23 |
| 5,073,241 A | 12/1991 | Watanabe | 204/192.15 |
| 5,073,450 A | 12/1991 | Nietering | 428/336 |
| 5,090,985 A | 2/1992 | Soubeyrand et al. | 65/60.52 |
| 5,106,671 A | 4/1992 | Amberger et al. | 428/215 |
| RE34,035 E | 8/1992 | Dimigen et al. | 428/244 |
| 5,139,633 A | 8/1992 | Kashida et al. | 204/192.15 |
| 5,171,414 A | 12/1992 | Amberger et al. | 204/192.26 |
| 5,190,807 A | 3/1993 | Kimock et al. | 428/216 |
| 5,201,926 A | 4/1993 | Szczyrbowski et al. | 65/60.2 |
| 5,209,996 A | 5/1993 | Kashida et al. | 430/5 |
| 5,211,759 A | 5/1993 | Zimmermann et al. | 118/723 |
| 5,245,468 A | 9/1993 | Demiryont et al. | 359/359 |
| 5,284,539 A | 2/1994 | McKernan et al. | 156/154 |
| 5,286,524 A | 2/1994 | Slutz et al. | 427/249 |
| 5,302,449 A | 4/1994 | Eby et al. | 428/336 |
| 5,318,830 A | 6/1994 | Takamatsu et al. | 428/216 |
| 5,346,600 A | 9/1994 | Nieh et al. | 204/192.3 |
| 5,366,764 A | 11/1994 | Sunthankar | 427/248.1 |
| 5,378,527 A | 1/1995 | Nakanishi et al. | 428/216 |
| 5,394,269 A | 2/1995 | Takamatsu et al. | 359/580 |
| 5,401,543 A | 3/1995 | O'Neill et al. | 427/580 |
| 5,415,756 A | 5/1995 | Wolfe et al. | 204/192.23 |
| 5,424,130 A | 6/1995 | Nakanishi et al. | 428/410 |
| 5,453,459 A | 9/1995 | Roberts | 524/123 |
| 5,470,661 A | 11/1995 | Bailey et al. | 428/408 |
| 5,476,713 A | 12/1995 | Abiko et al. | 428/332 |
| 5,482,602 A | 1/1996 | Cooper et al. | 204/192.11 |
| 5,498,475 A | 3/1996 | Takigawa et al. | 428/334 |
| 5,507,930 A | 4/1996 | Yamashita et al. | 204/192.15 |
| 5,520,996 A | 5/1996 | Balian et al. | 428/216 |
| 5,529,631 A | 6/1996 | Yoshikawa et al. | 118/718 |
| 5,558,751 A | 9/1996 | Mahler et al. | 204/298.26 |
| 5,569,501 A | 10/1996 | Bailey et al. | 427/577 |
| 5,594,585 A | 1/1997 | Komatsu | 359/512 |
| 5,595,825 A | 1/1997 | Guiselin | 428/428 |
| 5,597,622 A | 1/1997 | Zö ller et al. | 427/563 |
| 5,605,609 A | 2/1997 | Ando et al. | 204/192.23 |
| 5,607,723 A | 3/1997 | Plano et al. | 427/249 |
| 5,618,590 A | 4/1997 | Naruse et al. | 427/528 |
| 5,624,760 A | 4/1997 | Collins et al. | 428/426 |
| 5,633,208 A | 5/1997 | Ishikawa | 438/699 |
| 5,643,423 A | 7/1997 | Kimock et al. | 204/192.35 |
| 5,643,432 A | 7/1997 | Qiu | 205/50 |
| 5,645,699 A | 7/1997 | Sieck | 204/192.12 |
| 5,645,900 A | 7/1997 | Ong et al. | 427/571 |
| 5,669,144 A | 9/1997 | Hahn et al. | 30/346.54 |
| 5,674,625 A | 10/1997 | Takahashi et al. | 428/428 |
| 5,679,431 A | 10/1997 | Chen et al. | 428/65.3 |
| 5,683,561 A | 11/1997 | Hollars et al. | 204/298.25 |
| 5,698,262 A | 12/1997 | Soubeyrand et al. | 427/255.3 |
| 5,723,172 A | 3/1998 | Sherman | 427/109 |
| 5,733,660 A | 3/1998 | Makita et al. | 428/426 |
| 5,733,669 A | 3/1998 | Veyhl et al. | 428/698 |
| 5,745,291 A | 4/1998 | Jenkinson | 359/526 |
| 5,762,674 A | 6/1998 | Maltby, Jr. et al. | 65/60.1 |
| 5,763,087 A | 6/1998 | Falabella | 428/408 |
| 5,780,119 A | 7/1998 | Dearnaley et al. | 427/528 |
| 5,789,040 A | 8/1998 | Martinu et al. | 427/575 |
| 5,814,196 A | 9/1998 | Hollars et al. | 204/298.15 |
| 5,820,994 A | 10/1998 | Gotoh et al. | 428/451 |
| 5,830,327 A | 11/1998 | Kolenkow | 204/192.12 |
| 5,830,332 A | 11/1998 | Babich et al. | 204/192.15 |
| 5,846,613 A | 12/1998 | Neuville | 427/575 |
| 5,854,708 A | 12/1998 | Komatsu et al. | 359/512 |
| 5,888,593 A | 3/1999 | Petrmichl et al. | 427/563 |
| 5,972,184 A | 10/1999 | Hollars et al. | 204/298.09 |
| 6,074,981 A | 6/2000 | Tada et al. | 502/224 |
| 6,156,171 A | 12/2000 | Hollars et al. | 204/298.25 |
| 6,165,598 A | 12/2000 | Nelson | 428/212 |
| 6,165,616 A | 12/2000 | Lemelson et al. | 428/408 |
| 6,210,750 B1 | 4/2001 | Cho et al. | 427/190 |
| 6,261,693 B1 | 7/2001 | Veerasamy | 428/408 |
| 6,270,633 B1 * | 8/2001 | Onaka et al. | 204/192.12 |
| 6,299,981 B1 | 10/2001 | Azzopardi et al. | 428/429 |
| 6,333,084 B1 | 12/2001 | Woodard et al. | 428/34 |
| 6,365,010 B1 | 4/2002 | Hollars | 204/192.12 |
| 2002/0155265 A1 * | 10/2002 | Choi et al. | 428/212 |

* cited by examiner

SOIL-RESISTANT COATING FOR GLASS SURFACES

CROSS-REFERENCE TO RELATED APPLICATIONS

The present application is a continuation of U.S. application Ser. No. 09/599,301, filed 12 Jun. 2000, now U.S. Pat. No. 6,660,365, which claims priority to U.S. provisional application Ser. No. 60/168,497 filed 02 Dec. 1999. U.S. application Ser. No. 09/599,301, filed 21 Jun. 2000, now U.S. Pat No. 6,660,365 is a continuation-in-part of PCT/US99/02208 filed 02 Feb. 1999, which claims priority to U.S. provisional application Ser. No. 60/113,259, filed 21 Dec. 1998. The entire teachings of each prior patent and patent application identified in this paragraph are incorporated herein by reference.

FIELD OF THE INVENTION

The present invention provides a coating for glass substrates and the like which resist accumulation of dirt and water stains. Coated glass substrates of the invention can be used in insulated glass units wherein the coating of the invention is carried on an exterior surface of one pane of glass while a reflective coating is applied on the opposite side of the same pane of glass.

BACKGROUND OF THE INVENTION

Keeping windows and other glass surfaces clean is a relatively expensive, time-consuming process. While cleaning any individual window is not terribly troublesome, keeping a larger number of windows clean can be a significant burden. For example, with modern glass office towers, it takes significant time and expense to have window washers regularly clean the exterior surfaces of the windows.

Windows and other glass surfaces can become "dirty" or "soiled" in a variety of ways. Two of the primary manners in which windows can collect dirt involve the action of water on the glass surface. First, the water itself can deposit or collect dirt, minerals or the like onto the surface of the glass. Obviously, dirty water landing on the glass will leave the entrained or dissolved dirt on the glass upon drying. Even if relatively clean water lands on the exterior surface of a window, each water droplet sitting on the window will tend to collect dust and other airborne particles as it dries. These particles and any other chemicals which become dissolved in the water will become more concentrated over time, leaving a characteristic spot or drying ring on the glass surface.

The second way in which water tends to give a window or other glass surface a soiled or less attractive appearance is tied to an attack on the glass surface itself. As a droplet of even relatively clean water sits on a glass surface, it will begin to leach alkaline components from the glass. For a typical soda lime glass, the soda and lime will be leached out of the glass, increasing the pH of the droplet. As the pH increases, the attack on the glass surface will become more aggressive. As a result, the glass which underlies a drying water droplet will become a little bit rougher by the time the water droplet completely dries. In addition, the alkaline components which were leached out of the glass will be redeposited on the glass surface as a drying ring. This dried alkaline material not only detracts from the appearance of the glass; it will also tend to go back into solution when the glass surface is wetted again, rapidly increasing the pH of the next water droplet to coalesce on the glass surface.

In storing and shipping plate glass, the presence of water on the surfaces between adjacent glass sheets is a chronic problem. One can take steps to shield the glass from direct contact with water. However, if the glass is stored in a humid environment, water can condense on the glass surface from the atmosphere.

This becomes more problematic when larger stacks of glass are collected. Large stacks of glass have a fairly large thermal mass and will take a long time to warm up. As a consequence, they will often be cooler than the ambient air when ambient temperature increases (e.g., in the morning), causing moisture in the air to condense on the surface of the glass. Due to limited air circulation, any moisture which does condense between the sheets of glass will take quite a while to dry. This gives the condensed moisture a chance to leach the alkaline components out of the glass and adversely affect the glass surface. The rate of attack can be slowed down somewhat by applying an acid to the surface of the glass. This is commonly done by including a mild acid, e.g., adipic acid, in the separating agent used to keep glass sheets from sticking to and scratching one another.

A number of attempts have been made to enable a glass sheet to keep a clean appearance longer. One avenue of current investigation is a "self-cleaning" surface for glass and other ceramics. Research in this area is founded on the ability of certain metal oxides to absorb ultraviolet light and photocatalytically break down biological materials such as oil, plant matter, fats and greases, etc. The most powerful of these photocatalytic metal oxides appears to be titanium dioxide, though other metal oxides which appear to have this photocatalytic effect include oxides of iron, silver, copper, tungsten, aluminum, zinc, strontium, palladium, gold, platinum, nickel and cobalt.

While such photocatalytic coatings may have some benefit in removing materials of biological origin, their direct impact on other materials is unclear and appears to vary with exposure to ultraviolet light. As a consequence, the above-noted problems associated with water on the surface of such coated glasses would not be directly addressed by such photocatalytic coatings.

A number of attempts have been made to minimize the effect of water on glass surfaces by causing the water to bead into small droplets. For example, U.S. Pat. No. 5,424,130 (Nakanishi, et al., the teachings of which are incorporated herein by reference) suggests coating a glass surface with a silica-based coating which incorporates fluoroalkyl groups. The reference teaches applying a silicone alkoxide paint onto the surface of the glass, drying the paint and then burning the dried paint in air. Nakanishi, et al. stress the importance of substituting part of the non-metalic atoms, i.e., oxygen in a layer of $SiO_2$, with a fluoroalkyl group. Up to 1.5% of the oxygen atoms should be so substituted. Nakanishi, et al. state that if less than 0.1% of the oxygen atoms are substituted with a fluoroalkyl group, the glass won't repel water properly because the contact angle of water on the glass surface will be less than 80°.

Such "water repellent" coatings do tend to cause water on the surface of the glass to bead up. If the coating is applied to an automobile windshield or the like where a constant flow of high velocity air is blowing over the surface, this water beading effect can help remove water from the glass surface by allowing the droplets to blow off the surface. However, in more quiescent applications, these droplets will tend to sit on the surface of the glass and slowly evaporate. As a consequence, this supposed "water repellent" coating will not solve the water-related staining problems noted above. To the contrary, by causing the water to bead up more readily, it may actually exacerbate the problem.

Other silica coatings have been applied to the surface of glass in various fashions. For example, U.S. Pat. No. 5,394,269 (Takamatsu, et al.) proposes a "minutely rough" silica layer on the surface of glass to reduce reflection. This roughened surface is achieved by treating the surface with a supersaturated silica solution in hydrosilicofluoric acid to apply a porous layer of silica on the glass sheet. By using a multi-component of sol gel solution, they claim to achieve a surface which has small pits interspersed with small "islet-like land regions" which are said to range from about 50–200 nm in size. While this roughened surface may help reduce reflection at the air/glass interface, it appears unlikely to reduce the water-related staining problems discussed above. If anything, the porous nature of this coating appears more likely to retain water on the surface of the glass. In so doing, it seems probable that the problems associated with the long-term residence of water on the glass surface would be increased.

SUMMARY OF THE INVENTION

In one aspect, the present invention provides a glass article which has a water-sheeting coating and a method of applying such a coating. In accordance with a first embodiment of this invention, a glass article has at least one coated surface bearing a water-sheeting coating. This water-sheeting coating comprises silica sputtered directly onto an exterior surface of the glass. The water-sheeting coating has an exterior face which is substantially non-porous, but which has an irregular surface. This water-sheeting coating desirably reduces the wetting angle of water on the coated surface of the glass article below about 25° and causes water applied to the coated surface of the glass article to sheet.

In accordance with a second embodiment of the invention, a window is provided having at least one pane of glass having an exterior surface exposed to periodic contact with water. The exterior surface of this pane of glass has a water-sheeting coating comprising silica sputtered directly on the glass surface to a mean thickness of between about 15 Å and about 350 Å. This water-sheeting coating has an exterior face which is substantially non-porous, but which has an irregular surface. The water-sheeting coating causes water applied to the coated surface of the pane of glass to sheet.

In a further embodiment of the invention, a sheet of glass has an interior surface bearing a reflective coating thereon and an exterior surface bearing a water-sheeting coating thereon. The reflective coating may comprise a reflective metal layer and at least one dielectric layer. The water-sheeting coating again comprises silica sputtered directly onto the exterior surface of the sheet of glass and this water-sheeting coating has an exterior face which is substantially non-porous, but which has an irregular surface. This water-sheeting coating desirably reduces the contact angle of water on the coated surface of the sheet of glass below about 25° and causes water applied to the coated exterior surface of the pane to sheet.

As noted above, the present invention also contemplates a method of rendering a glass surface resistant to soiling and staining. In one embodiment, the method comprises first providing a sheet of glass having an interior surface and an exterior surface. The interior and exterior surfaces of the glass are cleaned. Thereafter, the interior surface of the sheet of glass is coated with a reflective coating by sputtering, in sequence, at least one first dielectric layer, at least one metal layer, and at least one second dielectric layer. The exterior surface of the glass is coated with a water-sheeting coating by sputtering silica directly onto the exterior surface of the sheet of glass. If so desired, the water-sheeting coating can be applied on the same sputter coating apparatus used to create the reflective coating. With appropriate material selection, the water-sheeting coating and one of the dielectric layers of the reflective coating may even be applied in the same sputtering chamber in an oxidizing atmosphere. If so desired, the pane of glass can be coated on both the interior surface and the exterior surface while maintaining the glass in a constant orientation wherein the interior surface is positioned above the exterior surface.

In accordance with an alternative method of the invention, a sheet of glass having an interior surface and an exterior surface is provided. A sputtering line is also provided, the sputtering line comprising a series of sputtering chambers, each having a support for a sheet of glass therein. At least one of the sputtering chambers comprises a dual direction sputtering chamber having an upper target position above the support and a lower target position below the support. The interior and exterior surface of the glass are cleaned and, thereafter, the sheet of glass is positioned on the support in the dual direction supporting chamber such that the interior surface is oriented toward the upper target and the exterior surface is oriented toward the lower target. The upper target is sputtered to deposit a dielectric layer. This dielectric layer may be deposited directly on the interior surface of the glass or on a film stack layer previously deposited on the interior surface of the glass. While the sheet of glass remains in the dual direction sputtering chamber, the lower target is sputtered to deposit a water-sheeting coating on the exterior surface of the glass. In one possible preferred embodiment, both the upper target and the lower target are sputtered in an oxidizing atmosphere within the same sputtering chamber.

In yet another embodiment, the invention provides a method of coating two sides of a single pane of glass or other substrate in a single pass through a coating apparatus, regardless of the nature of the coating being applied to either side of the glass. In this method, a sheet of glass (or other substrate) having a clean interior surface and a clean exterior surface is provided. A sputtering line is also provided, this line comprising a series of sputtering chambers each having a support for a sheet of glass therein, at least one of the sputtering chambers comprising a downward sputtering chamber having an upper target positioned above the support. A second of the sputtering chambers comprises an upward sputtering chamber having a lower target positioned below the support. The sheet of glass or other substrate is positioned on the support in the downward sputtering chamber such that the interior surface is oriented toward the upper target. The upper target is sputtered to deposit a coating directly on one of the interior surface of the glass or a film stack layer previously deposited on the interior surface of the glass. The sheet of glass is also positioned on the support in the upward sputtering chamber such that the exterior surface is oriented toward the lower target. The lower target is sputtered to deposit a coating on one of the exterior surface of the glass or a film stack layer previously deposited on the exterior surface of the glass. The glass is coated on both the interior surface and the exterior surface while maintaining a constant orientation wherein the interior surface is positioned above the exterior surface.

In still another embodiment, there is provided a glass article with an interior surface and an exterior surface. The interior surface bears a first water-sheeting coating and the exterior surface bears a second water-sheeting coating. The first and second water-sheeting coatings each comprise silica sputtered directly onto the respective surface of the glass article and each has an exterior face that is substantially non-porous but has an irregular surface. The first and second water-sheeting coatings each reduce the contact angle of water on the respective surfaces below 25° and cause water applied thereto to sheet.

In another embodiment, a multi-pane insulated glass unit is provided. The unit includes first and second panes of glass held in a spaced-apart relationship by a spacer to define a sealed interpane space. The first pane has an exterior surface oriented away from the second pane. This exterior surface is also exposed to periodic contact with water. The second pane has an interior surface exposed to the interpane space and an exterior surface oriented away from the first pane. A first water-sheeting coating is carried on the exterior surface of the first pane. A second water-sheeting coating is carried on the exterior surface of the second pane. The first and second water-sheeting coatings each comprising silica sputtered directly onto the respective surface of the first and second panes. The first and second water-sheeting coatings each have an exterior face that is substantially non-porous but has an irregular surface. The first and second water-sheeting coatings each reduce the contact angle of water on the respective surface of the first and second panes to below 25° and cause water applied thereto to sheet.

In yet another embodiment, there is provided a method of rendering surfaces of a pane of glass resistant to soiling and staining. A sheet of glass having a clean interior surface and a clean exterior surface is provided. Silica is sputtered directly onto the interior surface of the sheet of glass to yield a first water-sheeting coating having a contact angle with water below about 25° which causes water applied to said interior surface to sheet. Silica is also sputtered directly onto the exterior surface of the sheet of glass to yield a second water-sheeting coating having a contact angle with water below about 25° which causes water applied to said exterior surface to sheet.

In still another embodiment, a method of coating two sides of a pane of glass in a single pass through a coating apparatus is provided. A sheet of glass having a clean first surface and a clean second surface is provided. A sputtering chamber having a plurality of rollers that define a substrate support therein is provided. The chamber has an upper target positioned above the support that is adapted to downwardly sputter. The chamber also has a lower target positioned below the support that is adapted to upwardly sputter. The sheet of glass is positioned in the chamber such that the first surface of the sheet of glass rests on one or more of the rollers and is oriented toward the lower target. With the sheet of glass in this position, the second surface of the sheet of glass is oriented toward the upper target. The lower target is sputtered to deposit a first water-sheeting coating on the first surface of the glass. The first water-sheeting coating has a contact angle with water below about 25° which causes water applied to said first surface to sheet. The upper target is sputtered to deposit a second water-sheeting coating on the second surface of the glass. The second water-sheeting coating has a contact angle with water below about 25° which causes water applied to said second surface to sheet.

In another embodiment, there is provided a method of rendering a glass surface resistant to soiling and staining. A sheet of glass having a clean interior surface and a clean exterior surface is provided. A sputtering line comprising a series of sputtering chambers is provided. Each sputtering chamber in the line has a plurality of rollers that define a substrate support. The sputtering line includes an upward sputtering chamber with a lower target positioned below the rollers in that chamber. The sheet of glass of positioned in the upward sputtering chamber such that the exterior surface of the sheet of glass rests on two or more of the rollers in that chamber. The lower target is sputtered to deposit silica directly onto the exterior surface of the glass to yield a water-sheeting coating having a contact angle with water below about 25° which causes water applied to the exterior surface to sheet. The sputtered silica travels between said two or more rollers before being deposited on the exterior surface of the sheet of glass.

DETAILED DESCRIPTION OF THE PREFERRED EMBODIMENTS

Figure 1:
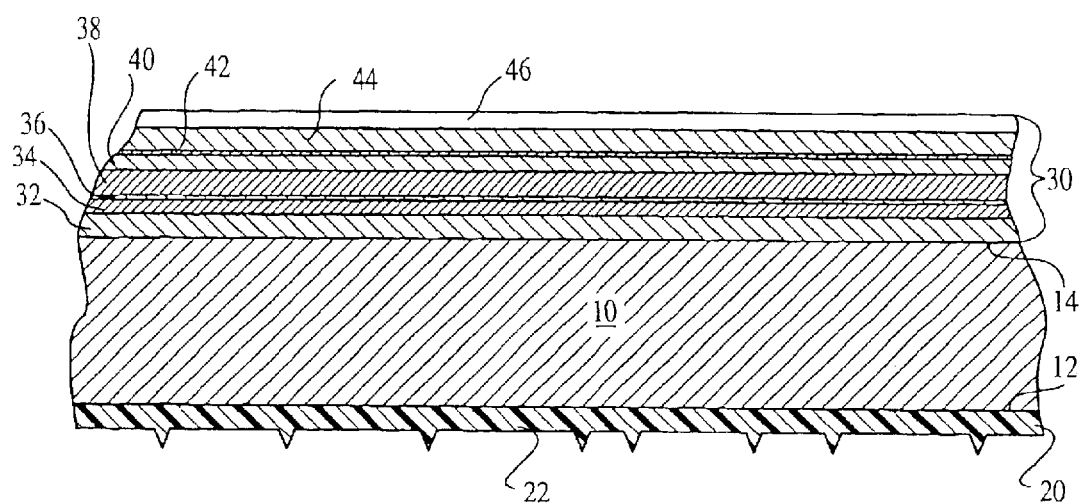
FIG. 1 is a schematic cross-sectional view of a sheet of glass bearing a coating in accordance with the invention.

FIG. 1 schematically illustrates a sheet of glass bearing a pair of coatings in accordance with one useful embodiment of the invention. The sheet of glass 10 includes an exterior face 12 and an interior face 14. (The designation of "interior" and "exterior" face in the ensuing discussion is somewhat arbitrary. It is assumed, though, that in most circumstances the exterior face will be exposed to an ambient environment wherein it may come into contact with dirt, water and the like. The interior face may also be oriented toward the same kind of ambient environment, as where a sheet of glass is used as a shower door. In such cases, it would be desirable to provide a water-sheeting coating of this invention on both the interior and exterior faces of the sheet of glass (not shown). In the embodiments illustrated in FIGS. 2 and 3, though, this "interior" face is actually protected and a second pane of glass stands between this interior face and the ambient environment.)

In FIG. 1, the interior face 14 of the glass 10 bears a reflective coating 30. As those skilled in the art will readily recognize, this reflective coating may take any desired form depending on the desired properties. A wide variety of such films are known in the art and the precise nature of the reflective coating 30 will vary depending on the application for which the glass article is used. Several particularly useful and advantageous reflective coatings are discussed below, but others will be apparent to those in the field.

If, for example, the glass article is to be used as a mirror, the coating 30 may simply comprise a relative thick layer of a reflective metal. If so desired, a protective coating of a dielectric material may be applied over the surface of the metal opposite the surfacing contact with the glass. As is known in the art, this will help protect the metal layer from chemical and physical attack. One could also employ any of a variety of mirror coatings known in the art which comprise a layer of a dielectric on either side of a reflective metal layer; many dichroic mirrors known in the art employ such a In the embodiment of FIG. 1, the reflective coating 30 is typified as an infrared reflective coating of the type commonly used in low emissivity solar control films. Typically, such films will comprise a metal layer sandwiched between a pair of dielectric layers. This structure may be repeated to further enhance the infra-reflective properties of the film stack. One example of a useful infrared reflective film stack is disclosed in U.S. Pat. No. 5,302,449 (Eby, et al.), the teachings of which are incorporated herein by reference.

The illustrative film stack 30 of FIG. 1 (referred to in Table 1 below as coating A) includes a base coat 32 which may comprise one or more layers of dielectric materials. For example, this base coat 32 may comprise zinc oxide applied at a thickness of about 150–275 Å. A first metal layer 34 may be applied directly on top of this base coat 32. This metal may be, for example, silver applied at a thickness of between about 100 Å and about 150 Å. A second dielectric layer 38 may be applied over the first metal layer 34. The thickness of this dielectric layer 38 will depend, at least in part, on whether a second metal layer 40 will be included in the film stack. In a film stack having two metal layers, as shown, this second dielectric layer 38 may typically comprise a relatively thick layer of a metal oxide, such as 700–750 Å of zinc oxide. If so desired, a relatively thin sacrificial layer 36 may be applied between the metal layer 34 and the dielectric layer 38. This will help protect the metal layer 34 during the sputter deposition of the dielectric layer 38. The sacrificial layer 36 may, for example, comprise a layer of titanium metal applied at a thickness of 25 Å or less. This titanium metal will oxidize sacrificially (yielding an oxidized titanium denoted as "$TiO_x$" in Table 1) during the application of a metal oxide dielectric 38, limiting any damage to underlying silver layer 34.

In the film stack illustrated in FIG. 1 (referred to below as coating A), a second metal layer 40 is applied over the second dielectric layer 38. The second metal layer 40 will usually be made of the same material as is the first metal layer 34. For example, this second metal layer 40 may comprise about 125–175 Å of silver. Again, a sacrificial layer 42 of titanium or the like may be applied over the metal layer 40 to protect the metal layer during subsequent deposition of the overlying dielectrics 44 and 46. A third dielectric layer 44 is applied over the sacrificial layer 42. This dielectric layer 44 can also be a metal oxide, e.g., zinc oxide applied at about 250–300 Å. If so desired, a protective overcoat 46 of another dielectric material can be applied over the dielectric layer 44. In one preferred embodiment, this overcoat 46 may comprise a 50–60 Å layer of $Si_3N_4$.

Alternative film stacks may be preferred for different applications. For example, various low emissivity film stacks may be applied to the interior face of the glass. Six preferred low emissivity film stacks (identified as coatings B-G) will be described. These six film stacks are also summarized in Table 1 following their description below.

Coating B comprises a layer of zinc oxide sputtered directly onto the interior face of the glass to a thickness of about 125 Å. Silver is applied over this zinc oxide layer to a thickness of about 105 Å. A thin coating of titania (applied as a sacrificial titanium layer which subsequently oxidizes, at least partially, as described above) is deposited over the silver layer to a thickness of about 25 Å. A second zinc oxide layer is applied over the titania layer to a thickness of about 370 Å. Finally, an outer coating of silicon nitride is sputtered onto the second zinc oxide layer to a thickness of about 60 Angstroms. This coating as reflective layer 30 in combination with a water-sheeting coating in accordance with the invention yields a particularly attractive product to meet consumer demands.

In alternative coating C, the first three sputtered layers are the same as those of coating B (i.e., 125 Å zinc oxide, 105 Å silver, and 25 Å titania). A second zinc oxide layer is sputtered onto the titania to a thickness of about 200 Å. A silicon nitride layer is applied over this second zinc oxide layer to a thickness of about 80 Å. A third zinc oxide layer is then deposited over the silicon nitride layer to a thickness of about 105 Å. Finally, a second layer of silicon nitride is sputtered onto the third zinc layer to a thickness of about 60 Å. Use of this coating as reflective layer 30 in combination with a water-sheeting coating according to the present invention yields an especially attractive and useful product that satisfies the demands of consumers and those in the field.

A third alternative film stack, denoted coating D, comprises a zinc oxide layer sputtered directly onto the interior face of the glass to a thickness of about 190 Å. Silver is applied over this zinc oxide layer to a thickness of about 75 Å. Next, a relatively thin layer of titania is applied to a thickness of about 25 Å. Over this titania layer is applied a second layer of zinc oxide to a thickness of about 735 Å. A second layer of silver is deposited over the second layer of zinc oxide to a thickness of about 135 Å. A second thin layer of titania is then applied over the second layer of silver to a thickness of about 25 Å. A third coating of zinc oxide is then applied over the second layer of titania to a thickness of about 200 Å. Finally, an outer coating of silicon nitride is applied over the second layer of titania to a thickness of about 85 Å. Employing this coating as reflective layer 30 in connection with the water-sheeting coating of the present invention gives an outstanding product that has unique qualities that are highly useful to many consumers.

In alternative coating E, the first three sputtered layers are the same as those of coating D (i.e., 190 Å zinc oxide, 75 Å silver, and 25 Å titania). Over the titania layer is applied a second layer of zinc oxide to a thickness of about 435 Å. A silicon nitride layer is deposited over this second zinc oxide layer to a thickness of about 80 Å. A third layer of zinc oxide is then deposited over the silicon nitride layer to a thickness of about 220 Å. A second layer of silver is then applied over the third zinc oxide layer to a thickness of about 135 Å. Next, a second relatively thin layer of titania is applied over the second layer of silver to a thickness of about 25 Å fourth layer of zinc oxide is then deposited over this second layer of titania to a thickness of about 200 Å. Finally, an outer layer of silicon nitride is deposited over the fourth layer of zinc oxide to a thickness of about 85 Å. Applying this coating as reflective layer 30 in combination with a water-sheeting coating of the present invention gives an exceptional product that meets the particular requirements of many applications.

A fifth alternative film stack comprises a layer of zinc oxide sputtered directly onto the interior face of the glass to a thickness of about 165 Å. Over this zinc oxide layer is applied a silver layer to a thickness of about 110 Å. Next, a relatively thin layer of titania is deposited over this silver layer to a thickness of about 25 Å. A second zinc oxide layer is deposited over this titania layer to a thickness of about 745 Å. A second silver layer is then applied over the second zinc oxide layer to a thickness of about 125 Å. Over the second silver layer is applied a second relatively thin layer of titania to a thickness of about 25 Å. A third zinc oxide layer is deposited onto this second titania layer to a thickness of about 280 Å. Finally, an outer coating of silicon nitride is applied to a thickness of about 70 Å. This coating as reflective layer 30 in combination with a water-sheeting coating of this invention produces a particularly useful and attractive product that meets the requirements of many consumers.

In a sixth alternative film stack, the first three sputtered layers are the same as those of the film stack just discussed (i.e., 165 Å zinc oxide, 110 Å silver, and 25 Å titania). A second layer of zinc oxide is then deposited over the titania layer to a thickness of about 445 Å. Silicon nitride is then applied over the second zinc oxide layer to a thickness of about 80 Å. A third layer of zinc oxide is then applied over this silicon nitride layer to a thickness of about 220 Å. Next, a second layer of silver is deposited onto the third zinc oxide layer to a thickness of 125 Å. Over this second layer of silver is applied a second layer of titania to a thickness of about 25 Å. A fourth zinc oxide layer is then deposited onto the second silver layer to a thickness of about 280 Å. Finally, an outer coating of silicon nitride is applied over the fourth zinc oxide layer to a thickness of about 70 Å. When this coating is used as reflective layer 30 in conjunction with a water-sheeting coating of the present invention, the result is an exceptionally attractive product that is particularly useful in the applications of many consumers.

The water-sheeting coating 20 of the invention desirably comprises silica deposited directly on the exterior surface 12 of the glass 10. As will be discussed below in connection with FIGS. 8–10, the exterior face 22 of this coating 20 is substantially non-porous but has an irregular surface. (This is schematically shown as a series of irregularly-spaced and -sized spikes on the exterior face 22 of the coating 31). Accordingly, attributing any specific thickness to this coating 20 will be inherently somewhat inaccurate. However, the coating 20 desirably has a median thickness of between about 15 Å and about 350 Å, with a range of between about 15 Å and about 150 Å being preferred. The major benefit of this coating at the least cost is believed to be evidenced at a range of about 20 Å to about 120 Å. One preferred manner in which this coating 20 may be applied to the exterior surface 12 of the glass 10 will be discussed in more detail below.

Figure 2:
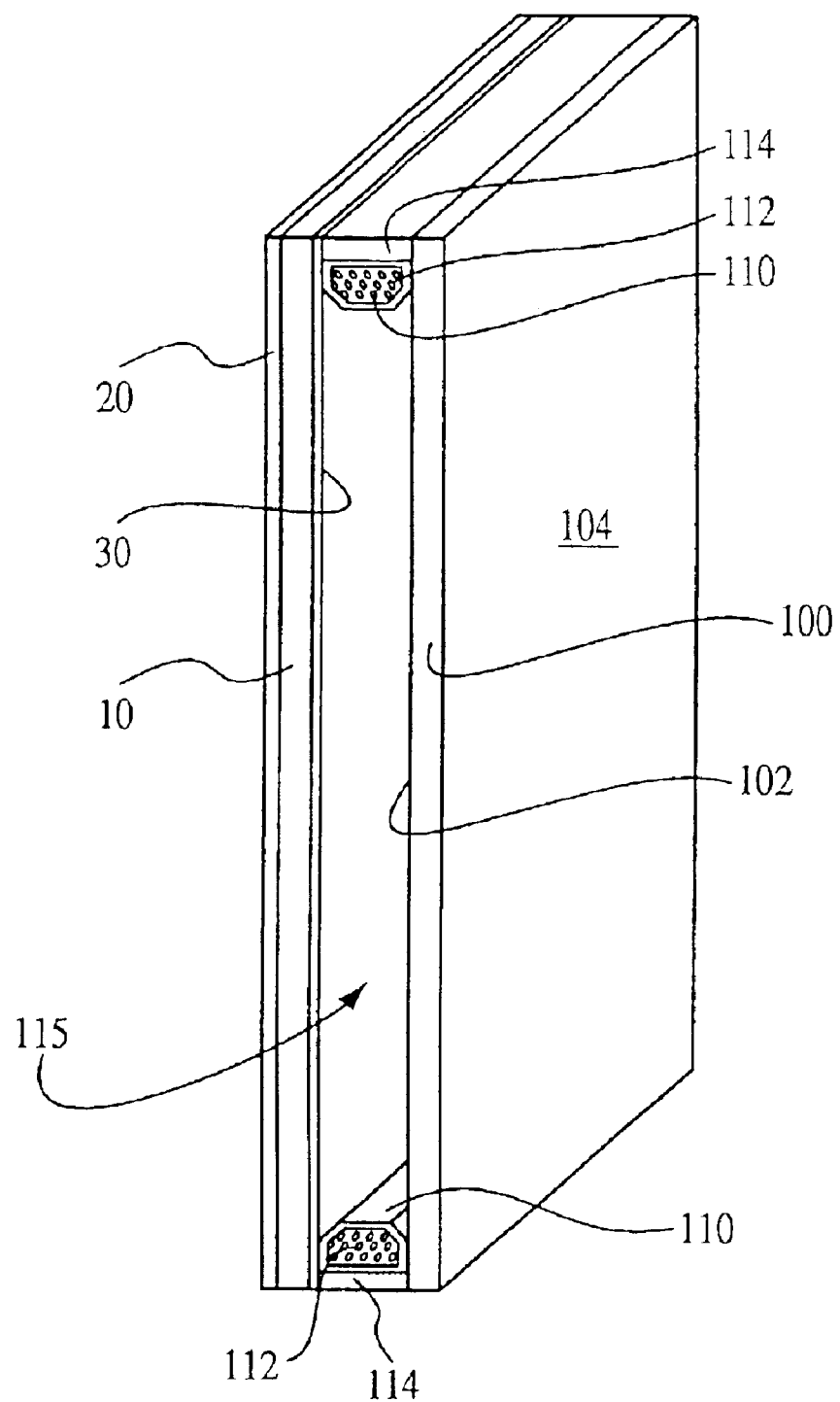
FIG. 2 is a schematic cross-sectional illustration of a multi-pane insulated glass unit incorporating a water-sheeting coating of the intervention.

FIG. 2 is a schematic illustration of a multi-pane insulated glass unit in accordance with a further embodiment of the invention. Insulated glass units are well known in the art and need not be discussed in any significant detail here. Briefly, though, such an insulated glass unit would generally comprise two panes of glass 10,100 held in a spaced-apart relationship by a spacer 110 to define a sealed interpane space 115 between the first pane 10 and the second pane 100. In the illustrated embodiment, the water-sheeting coating 20 carried by the exterior surface of the glass 10 is oriented away from the second pane of glass 100 while the reflective coating 30 carried by the interior face of the glass 10 is oriented toward the second pane of glass 100. The second pane of glass 100 has an interior surface exposed to the interpane space 115 and an exterior surface oriented away from the first pane of glass 10. If desired, a water-sheeting coating (not shown) may also be applied to the exterior surface 104 of the second pane of glass 100. This would render the exterior and surfaces of both panes of glass resistant to staining and soiling.

The spacer 110 is bonded on one side to the interior surface 102 of the second glass pane 100 and on the other

TABLE 1

| Coating A | Coating B | Coating C | Coating D | Coating E | Coating F | Coating G |
|---|---|---|---|---|---|---|
| 50–60 Å $Si_3N_4$ | 60 Å $Si_3N_4$ | 60 Å $Si_3N_4$ | 85 Å $Si_3N_4$ | 85 Å $Si_3N_4$ | 70 Å $Si_3N_4$ | 70 Å $Si_3N_4$ |
| 250–300 Å ZnO | 370 Å ZnO | 105 Å ZnO | 200 Å ZnO | 200 Å ZnO | 280 Å ZnO | 280 Å ZnO |
| ≦25 Å $TiO_x$ | 25 Å $TiO_x$ | 80 Å $Si_3N_4$ | 25 Å $TiO_x$ | 25 Å $TiO_x$ | 25 Å $TiO_x$ | 25 Å $TiO_x$ |
| 125–175 Å Ag | 105 Å Ag | 200 Å ZnO | 135 Å Ag | 135 Å Ag | 125 Å Ag | 125 Å Ag |
| 700–750 Å ZnO | 125 Å ZnO | 25 Å $TiO_x$ | 735 Å ZnO | 220 Å ZnO | 745 Å ZnO | 220 Å ZnO |
| ≦25 Å $TiO_x$ | Glass | 105 Å Ag | 25 Å $TiO_x$ | 80 Å $Si_3N_4$ | 25 Å $TiO_x$ | 80 Å $Si_3N_4$ |
| 100–150 Å Ag | | 125 Å ZnO | 75 Å Ag | 435 Å ZnO | 110 Å Ag | 445 Å ZnO |
| 150–275 Å ZnO | | Glass | 190 Å ZnO | 25 Å $TiO_x$ | 165 Å ZnO | 25 Å $TiO_x$ |
| Glass | | | Glass | 75 Å Ag | Glass | 110 Å Ag |
| | | | | 190 Å ZnO | | 165 Å ZnO |
| | | | | Glass | | Glass |

The water-sheeting coating 20 was applied to the inner surface 12 of the glass. It is preferred that this coating be applied directly on the surface of the glass sheet 12. As the glass, which will typically be a soda/lime glass, is largely formed of silica and the water-sheeting coating is also desirably formed of silica, this is believed to provide a strong bond between these two layers and may enhance the water-sheeting performance of the coating 20. In certain embodiments, it may be desirable to apply a water-sheeting coating directly onto both the inner and outer surfaces of the glass.

side to the first glass pane 10. As is known in the art, the spacer may be bonded directly to the interior surface 14 of the glass 10 or the reflective coating 30 may extend out to the margins of the glass 10 and the spacer may be attached directly to that coating 30.

Typically, the spacer will be formed of metal or the like and will have a desiccant 112 retained therein. This desiccant will be allowed to communicate with the gas in the interpane space 115 to remove any moisture which may seep between the panes of glass. An exterior seal 114 may be carried around the external periphery of the spacer 110 to form a reliable gas and moisture barrier.

Figure 3:
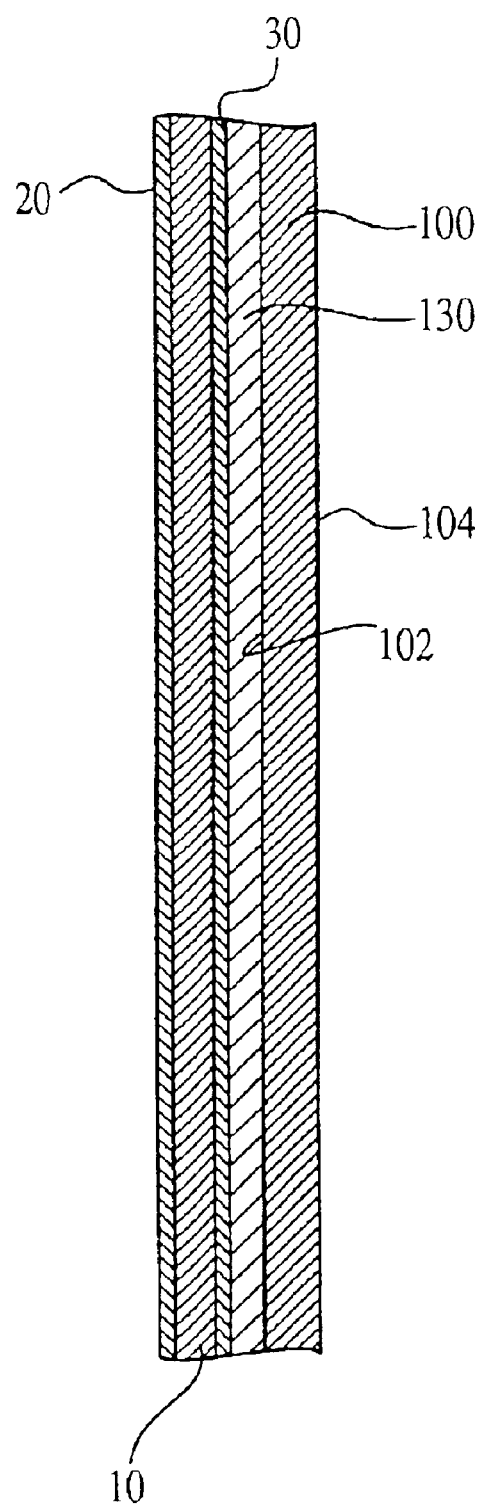
FIG. 3 is a schematic cross-sectional view of a laminated window structure of the type commonly used in automobile windshields bearing a water-sheeting coating of the invention.

FIG. 3 illustrates another application for a coated glass article of the invention. In this embodiment, the glass sheet 10 is bonded to a second sheet of glass 100 by an intermediate tear-resistant plastic film 130 to form a laminated structure. Such laminated window structures are well known in the field of automobile windows. Typically, this plastic layer 130 will take the form of a relatively thick layer of polyvinylbutyral or the like which is heat-fused to the other two sheets of glass. If so desired, the coating 30 may be omitted. More preferably, though, the reflective film 30 will comprise a heat-temperable infrared reflective film. A variety of such films are known in the art and the precise nature of this film is beyond the scope of the present invention, but any suitable heat-temperable coating 30 may be used. Laminated structures with an intermediate tear-resistant plastic film 130 may also be used as part of a shower door. Such shower doors may be more safe than plain glass doors, as the intermediate plastic film would tend to minimize glass shattering that might otherwise occur if the glass door were broken. In this case, it would be desirable to coat both the interior and the exterior surfaces of the door with a water-sheeting coating of the present invention. Both sides of a shower door would be expected to be in periodic contact with water due to the proximity of such doors to shower water and the high humidity produced by a shower.

As noted above, the water-sheeting coating is desirably applied by sputtering, as are the low emissivity coatings or the reflective coating 30, if present. These separate coatings can be applied using conventional sputtering equipment by applying the two coatings in separate passes through a sputtering line. For example, before the reflective coating is applied, the water-sheeting coating 20 of the invention can be applied to the exterior surface of the glass by positioning this surface of the glass beneath a silicon target in an oxidizing sputtering atmosphere. Thereafter, a multiple-layer reflective coating can be applied using a series of sputtering chambers in a conventional manner, with each chamber being adapted to sputter one or more specific layers of the desired film stack. Alternatively, a second water-sheeting coating can be sputtered directly onto the interior surface of the glass instead of such a reflective layer. One or both of the coated surfaces could then be exposed to periodic contact with water, whereby the water-sheeting coating would reduce soiling and staining of each exposed surface.

Figure 4:
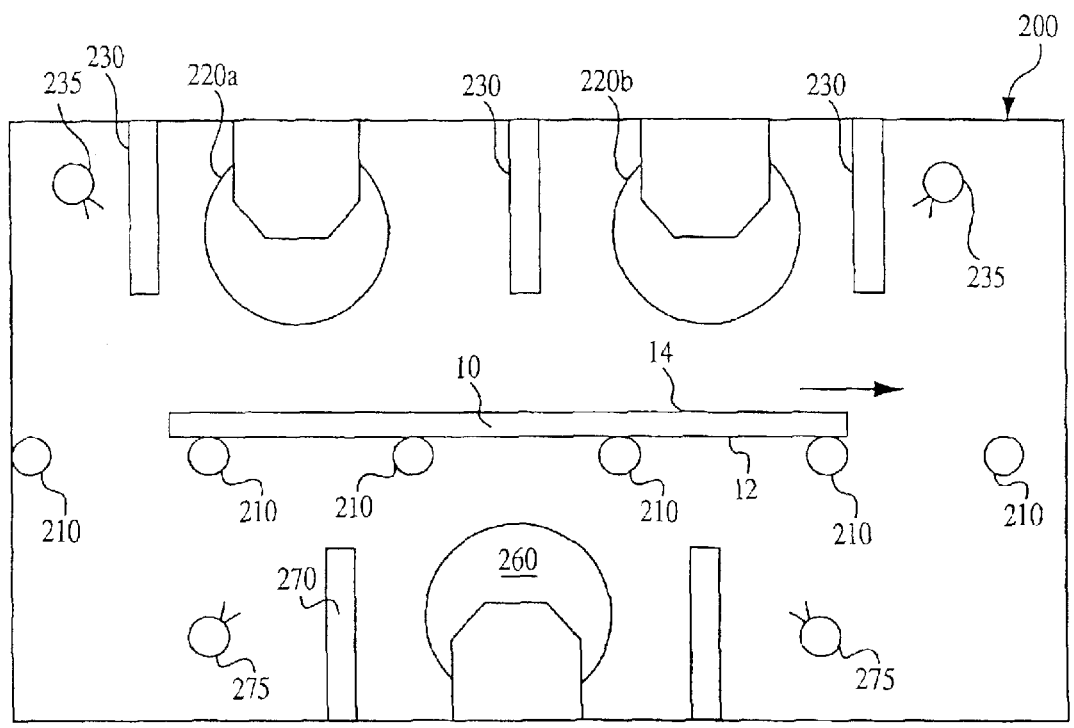
FIG. 4 is a schematic illustration of a dual direction sputtering chamber for use in accordance with the intervention.

FIG. 4 schematically illustrates a dual direction sputtering chamber in accordance with one embodiment of the present invention. Magnetron sputtering chambers are well known in the art and are commercially available from a variety of sources. While a thorough discussion of such magnetron sputtering chambers is beyond the scope of the present disclosure, one relatively useful structure for such a device is disclosed in U.S. Pat. No. 5,645,699 (Sieck), the teachings of which are incorporated herein by reference.

Generally speaking, though, magnetron sputtering involves providing a target formed of a metal or dielectric which is to be deposited on the substrate. This target is provided with a negative charge and a relatively positively charged anode is positioned adjacent the target. By introducing a relatively small amount of a desired gas into the chamber adjacent the target, a plasma of that gas can be established. Atoms in this plasma will collide with the target, knocking the target material off of the target and sputtering it onto the substrate to be coated. It is also known in the art to include a magnet behind the target to help shape the plasma and focus the plasma in an area adjacent the surface of the target.

In FIG. 4, the sheet of glass 10 to be coated is positioned on a plurality of support rollers 210 which are spaced along the length of the sputtering chamber 200. While the precise spacing of these rollers 210 can be varied, for reasons explained more fully below, it is desired that these rollers are spaced a little bit farther apart along at least a interim length of the chamber 200 to increase the effective coating area from the lower target 260.

In the illustrated embodiment, the sheet of glass 10 is oriented to travel horizontally across these rollers, e.g., from left to right. The interior surface 14 of the glass is oriented upwardly while the exterior surface 12 of the glass is oriented downwardly to rest on the rollers 210. (While this is probably the most typical configuration, it should be understood that the relative orientation of the glass within the sputtering chamber 200 can be switched so long as the relative positions of the upper targets 200a and 200b and the lower target 260 are also reversed. As a consequence, it should be noted that designating these targets as "upper" and "lower" targets is simply for purposes of convenience and the relative orientation of these elements within the sputtering chamber can be easily reversed if so desired.

The sputtering chamber 200 shown in FIG. 4 includes two spaced-apart upper sputtering targets 220a and 220b. While these targets can be planar targets, they are illustrated as being so-called rotary or cylindrical targets. These targets are arranged generally parallel to one another with a plurality of anodes 230 extending horizontally and generally parallel to these targets. As suggested in U.S. Pat. No. 5,645,699, an intermediate anode 230 may also be positioned between these two targets.

A gas distribution system is used to supply the sputtering gas to the chamber adjacent the targets 220a and 220b. While a variety of gas distribution systems are known in the art, this distribution system may simply comprise a pair of pipes 235 with a plurality of spaced-apart openings or nozzles oriented generally toward the target.

The use of multiple targets positioned above a glass substrate in a magnetron sputtering chamber is fairly conventional in the field. The unique aspect of the sputtering chamber 200 FIG. 4, though, is the presence of the "lower" target 260. This target is the target used to sputter the water-sheeting coating 20 of the invention directly on the exterior surface 12 of the glass. As with the upper targets 220a and 220b, the lower target 260 is provided with at least one, and preferably two, anodes 270 in sufficient proximity to establish a stable plasma. The gas distribution pipes 235 shown adjacent the upper targets 220a and 220b are undesirably far from the lower target 260 and the intermittent presence of the glass 10 will effectively divide the sputtering chamber 200 into two separate functional areas. Accordingly, it is preferred to have separate gas distribution pipes 275 positioned beneath the gas adjacent the lower target 260 to ensure a consistent supply of gas for the plasma adjacent the target. If so desired, the lower pipes 275 and the upper pipes 235 may be a part of the same gas distribution system, i.e., both sets of pipes can be connected to a single gas supply.

The nature of the gas supplied by the lower pipes 275 will depend at least in part on the nature of the sputtering target 260. In conventional magnetron sputtering, the target must serve as a cathode. Due to the dielectric nature of $SiO_2$, it can be exceedingly difficult to reliably sputter using a silica target. As a consequence, it is preferred that the target comprise silicon metal rather than silica. The material actually deposited on the exterior surface 12 of the glass can be converted to silica by including oxygen in the gas supplied through the lower gas distribution pipes 275.

While the successive sheets of glass 10 will effectively divide the sputtering chamber, this does not preclude gas introduced in one area of the chamber from travelling elsewhere in the chamber. As it is preferred that the lower target 260 comprise silicon metal sputtered in an oxidizing atmosphere, it is important that the sputtering of the upper targets 220a and 220b not be adversely affected by the presence of any excess oxygen which may be introduced through the lower pipes 275. This may effectively preclude the use of this dual direction sputtering chamber 200 to deposit a water-sheeting coating 20 on one side of the glass sheet and an oxygen-sensitive metal on the other surface. More advantageously, the dual direction sputtering chamber of FIG. 4 can be used to deposit a dielectric layer on the interior surface 14 of the glass and the silica water-sheeting coating 20 on the exterior surface 12 of the glass in a single chamber. The sputtered dielectric may be a nitride or the like so long as the introduction of some metal oxide into the nitride being deposited will not adversely affect the coating being applied. Ideally, though, the dielectric being applied to the interior surface 14 is an oxide (or at least a partial oxide) so that any commingling of the gases introduced through the two sets of pipes 235 and 275 will not adversely affect either the dielectric layer or the water-sheeting coating. For example, one or both of the targets 220a and 220b may be made of titanium metal or $TiO_x$ (where 1<X<2) and the gas introduced through both sets of gas distribution pipes 235 and 275 may comprise an appropriately balanced mixture of argon and oxygen.

In an alternative embodiment, the upper and lower targets in a sputtering chamber are both adapted to sputter water-sheeting coatings onto the sheet of glass. In this case, both targets may comprise silicon and may be sputtered in an oxidizing atmosphere. If desired, the upper and lower targets can be sputtered simultaneously to deposit silica on the interior and exterior surfaces of the glass at the same time.

In conventional magnetron sputtering chambers, the spacing of the rollers 210 used to support the glass is kept fairly small to permit smaller glass substrates to be processed on the line without any significant risk of having the glass fall between the rollers. In order to minimize the interference of the rollers in applying the water-sheeting coating on the exterior surface 12 of the glass, though, this spacing may be increased. The maximum safe spacing will need to be determined on a case-by-case basis for a given range of anticipated glass sizes. However, the larger the spacing between the rollers disposed in the path from the lower target 260 to the exterior surface 12 of the glass, the greater the percentage of the sputtered silica which will be deposited on the glass. Of course, the rollers in other areas of the sputtering apparatus can be maintained at their normal spacing. It may be desirable to make a few of the rollers in the dual direction sputtering chamber 200 easily removed so the chamber can be converted from the illustrated configuration to a more conventionally operated chamber coating only one side of the glass and having rollers spaced more closely together.

Instead of changing the spacing between the rollers, the rollers could instead be made smaller in diameter. Conventional rollers are hollow metal tubes. If so desired, the smaller diameter rollers can be stiffened, e.g., by filling them with a rigid foam. In order to maintain the same transport speed of the glass along the support, these smaller-diameter rollers would have to be turned more rapidly, e.g., by means of a pair of gears having the desired gear ratio.

The rollers 210 can be of any conventional structure. It has been found that good results can be obtained by employing cylindrical aluminum rollers about which a rope of Kevlar™ is spirally wound, with the Kevlar™ providing the surface with which the glass is in direct contact.

In one embodiment, there is provided a sputtering line comprising a series of sputtering chambers. Each sputtering chamber includes a plurality of rollers that define a continuous substrate support. At least one of these chambers is an upward sputtering chamber that includes a lower target positioned below the rollers in that chamber. A sheet of glass with a clean interior surface and a clean exterior surface is provided. The sheet is positioned in the upward sputtering chamber such that the exterior surface of the sheet of glass rests on one or more of the rollers in that chamber. The lower target is then sputtered to deposit silica directly onto the exterior surface of the glass. The sputtered silica is discharged from the lower target and travels between the rollers in the upward sputtering chamber before being deposited on the glass. This yields a water-sheeting coating having a contact angle with water below about 25° which causes water applied to the exterior surface to sheet.

In some specific applications, the dual direction sputtering chamber 200 of FIG. 4 may be sufficient to apply the entire desired coating to both the interior and exterior surfaces of the glass. More often, though, the sputtering chamber 200 would be part of a sputtering line comprising a series of sputtering chambers. Each sputtering chamber in the line could include both an upper target and a lower target, but in most conventional applications the film stack applied to the upper surface of the glass will be more complex (i.e. will comprise a series of distinct layers of varying composition) and thicker than is the water-sheeting coating of the invention. As a consequence, a majority of the sputtering chambers can comprise conventional, downward sputtering chambers having only an upper target, with no target positioned beneath the supports.

If the sputtering line comprises a combination of downward sputtering chambers and dual direction sputtering chambers 200, the position of the dual direction chambers along the sputtering line can be varied. If the water-sheeting coating of the invention is applied by sputtering a silicon-containing target (e.g., one formed primarily of silicon or formed of silicon doped with aluminum) in an oxidizing atmosphere, one should not attempt to deposit an oxidizable metal layer (e.g., an infrared reflective silver layer of the type conventionally used in low emissivity film stacks) on the upper surface of the glass in the same chamber. Accordingly, at least those chambers used to sputter a metal layer may be operated as a downward sputtering chamber by omitting the lower target. It would be possible, though, to deposit a metal oxide (e.g., $SiO_2$, $ZnO$ or $SnO_2$) on the upper surface of the glass in the same chamber.

Conventional wisdom would suggest to one skilled in the art that the water-sheeting coating of the invention be applied in the first sputtering chamber or, if necessary, the first several sputtering chambers to make sure that the water-sheeting coating is applied before the glass surface is damaged or soiled by contact with the rollers supporting the glass within the chambers. Quite surprisingly, it has been found that the opposite is true—the water-sheeting coating of the invention is optimally applied in the last sputtering chamber. If more than one dual direction sputtering chamber 200 is necessary to deposit a sufficiently thick water-sheeting coating without unduly slowing down glass speed through the sputtering line, the water-sheeting coating is optimally applied in the last few sputtering chambers.

If the water-sheeting coating of the invention is applied at the beginning of the sputtering line, the majority of the exterior surface of the glass will exhibit the desired water-sheeting properties. However, the margins of the glass may not exhibit these improved properties on a consistent basis. This is believed to be due to a slight overspray of the coating applied to the upper surface of the glass after deposition of the water-sheeting coating, wherein a very small amount of the material being applied to the upper surface will drift down to the lower surface and overlie the water-sheeting coating adjacent the edges of the glass sheet. While this oversprayed coating is thin enough as to have no readily discernable effect on the optical properties of the glass, this virtually invisible coating compromised the benefits of the water-sheeting coating around the edges of the glass. By applying the silica to the exterior surface of the glass toward the end of the sputtering line, the amount of overspray deposited on top of the silica coating can be minimized and the beneficial water-sheeting effects of this coating can be preserved. A dual direction sputtering chamber 200 such as that shown in FIG. 4 is believed to minimize the cost and maximize production efficiency in applying coatings to both sides of the sheet of glass. Less desirably, a water-sheeting coating of the invention could be applied in one pass while the reflective coating is applied to the other side of the glass in a second pass, flipping the glass between the passes to permit all of the targets to be positioned on the same side of the supports in the chamber(s). This is much less efficient than the process outlined above, though, and is not believed to be suitable for low-cost commercial glass production.

As the glass substrate moves through the chamber, there will be times when the glass does not effectively shield the upper targets 200a and 200b from the lower target 260 or vice versa. As a consequence, material from the upper targets will be deposited on the lower target and material from the lower target can be deposited on one or both of the upper targets. The sputtering chamber 200 of FIG. 4 is ideal if the upper targets 220a, 220b and the lower target 260 have substantially the same composition. If the upper targets have a different composition from the lower target, though, the cross-contamination of the different targets can lead to problems in sputtering or in maintaining consistent product quality.

At least in theory, this problem may be overcome by independently controlling the power supplied to each of the sputtering targets to ensure that each target is sputtering only when the glass is positioned to shield the upper and lower targets from one another. Current commercially available power supply controllers are not configured in this fashion, however. Furthermore, the control logic for such an arrangement can be unduly difficult if the sputtering line is used to coat glass substrates of varying sizes rather than a consistent size.

Figure 5:
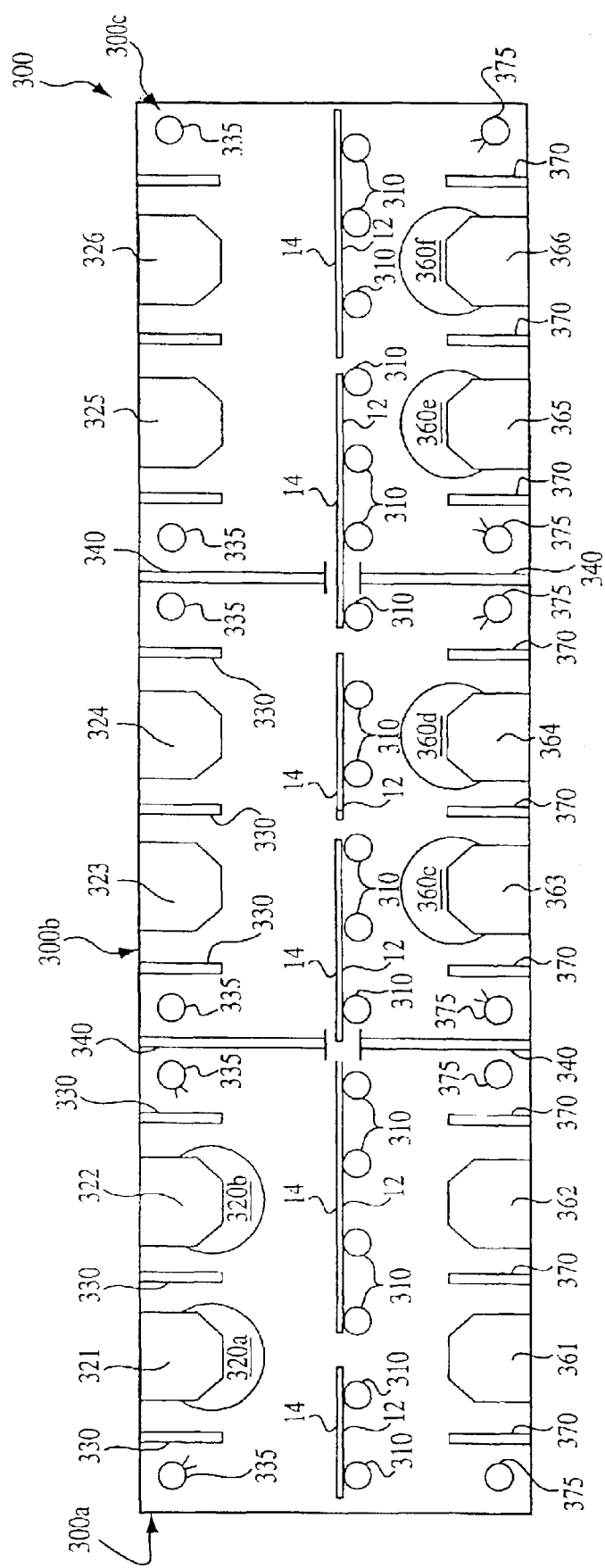
FIG. 5 is a schematic illustration of a multiple-zone dual direction sputtering chamber for use in accordance with another embodiment of the invention.

FIG. 5 illustrates one possible sputtering chamber 300 which can be used to coat both the interior surface 14 and the exterior surface 12 of the substrate in a single pass without significant cross contamination of the sputtering targets. Elements serving an analogous function to elements shown in FIG. 4 bear like reference numbers, but indexed by 100, e.g., the upper gas distribution pipes 335 of FIG. 5 are functionally analogous to the upper gas distribution pipes 235 of FIG. 4. The sputtering chamber 300 of FIG. 5 is effectively divided into three coating zones 300a, 300b and 300c by a pair of barriers 340. Some fraction of the gas in one coating zone may flow into another coating zone, so it is best to use a similar atmosphere in all three zones. However, the barriers 340 serve to effectively limit the amount of material sputtered in one coating zone which lands on a target in another coating zone. In the embodiment of FIG. 5, each of the three coating zones 300a–300c is adapted to hold up to four targets, with two targets positioned above the substrate and two positioned below the substrate. Hence, there are six upper target mounts 321–326 positioned above the path of the glass and six lower target mounts 361–366 positioned beneath the path of the glass. This allows maximum flexibility in using this single multi-zone sputtering chamber 300 to manufacture products having different properties. FIG. 5 schematically illustrates each of the upper target mounts 321–326 vertically aligned with one of the lower target mounts 361–366, respectively. It should be understood, however, that the targets need not be vertically aligned in this fashion and may be more advantageously positioned in a horizontally staggered arrangement.

In the configuration shown in FIG. 5, the first coating zone 300a has two upper targets (320a and 320b), but no lower targets on the lower target mounts 361 or 362. While a sputtering gas should be supplied to the upper gas distribution pipes 335 and power should be supplied to the upper anodes 330 in the first coating zone, there is no need to deliver any gas to the lower gas distribution pipes 375 or any power to the lower anodes 370. The second coating zone 300b has two lower targets 360c and 360d, but neither of the upper target mounts 323 and 324 carry sputtering targets. Similarly, the third coating zone 300c has two lower targets 360e and 360f, but neither of the upper target mounts 325 and 326 carry sputtering targets. Optimally (as discussed above), the first coating zone 300a is used to apply the outermost layer of the reflective film stack carried by the interior surface 14 of the substrates while the last two coating zones 300b and 300c are used to sputter the water-sheeting coating 20 on the exterior surface 12 of the substrates.

The arrangement of targets in the multiple-zone sputtering chamber 300 of FIG. 5 is merely illustrative and it should be understood that the target arrangement can be varied to maximize production efficiency for different products. For example, if a thicker water-sheeting coating is desired at the same glass speed, a silicon-containing target can be mounted on each of the lower target mounts 361–366 while none of the upper target mounts 321–326 carry a target. If a thinner coating will suffice (or if glass speed through the coating chamber is suitably reduced), only the last two lower target mounts 325 and 326 can be provided with targets while each of the first four upper target mounts 321–324 carry sputtering targets. Of course, any one or more of the coating zones 300a–300c can be operated much like the dual-direction sputtering chamber 200 of FIG. 4 by mounting targets in the upper and lower target mounts of the same zone.

The apparatus of FIGS. 4 and 5 and the method of depositing coatings using such coating systems is discussed in the present application primarily in the context of applying a reflective film stack on one side of the glass and a water-sheeting coating on the other side of the glass. It is to be understood, however, that this apparatus and method can be used to apply coatings to both sides of a pane of glass regardless of the nature of the coatings applied thereto. For example, the apparatus can be used to apply an anti-reflective coating on both sides of a pane of glass, to apply infrared reflective coatings to both sides of a transparent or translucent organic substrate, or to apply a water-sheeting coating to each side of the same substrate.

The advantage of the systems illustrated in FIGS. 4 and 5 is that a substrate can be provided with a sputtered coating (regardless of composition) on both sides in a single pass through the coating apparatus while the glass is maintained in a constant orientation, i.e., wherein it does not need to be flipped, turned or otherwise manipulated. This enables the use of a simple set of standard transport rollers 210 and 310 to move the glass along the production line. In the absence of the present invention, one typically would have to either manually handle the glass to flip it and send it back through the coating apparatus in a separate run, or use a complex glass handling system which must hold the substrate and flip it at some point during the production process. This enables glass having coatings on both sides to be produced particularly economically without any loss in coating quality. In the past, it was assumed that even if one were to coat the bottom side of the glass, contact with the rollers would mar that coating or and/or damage the bottom surface of the glass prior to application of the coating. Suprisingly, however, the present invention demonstrates that both sides of the glass can be coated in a single pass with excellent results.

The precise operating conditions (e.g. target composition, plasma composition, etc.) under which the water-sheeting coating of the invention is applied can be varied as necessary to optimize the deposition of a coating of the desired thickness. Given the present teaching as a guide, one of ordinary skill in the art should be able to select suitable operating conditions to apply a coating of the invention without undue experimentation.

A layer of $SiO_2$ in accordance with the invention may be sputter deposited using a silicon dioxide target in an inert atmosphere, but silica is a poor conductor and it can be difficult to sputter such dielectric materials in a DC sputtering apparatus. One could instead use a pure silicon target in an oxidizing atmosphere, but such targets are difficult to sputter in a consistent, controlled fashion because silicon is a semiconductor. To improve sputtering and reduce arcing, it is preferred that a target comprising silicon with about 5% aluminum be sputtered in an oxidizing atmosphere.

Even if an aluminum-doped silicon target is employed, the atmosphere in the sputtering chamber can be varied to achieve the optimum sputtering rate. While the sputtering atmosphere should be oxidizing, it need not be pure oxygen. To the contrary, a mixture of oxygen and an inert gas will enhance the sputtering rate. It is believed that a sputtering gas comprising oxygen and up to about 40% argon (preferably 0–20% argon) maintained at about $3 \times 10^{-3}$ mbar will suffice. The power applied to the sputtering target should be optimized to reduce arcing yet maximize sputtering rate. A power of up to about 80 kW should yield acceptable results.

One manufacturing arrangement which has been found to work well utilizes three rotary sputtering targets of silicon doped with about 5% aluminum, with a power of about 42 kW being applied to each target. The atmosphere in the sputtering chamber comprises 100% $O_2$ at a pressure of about 2.5–4.5 mTorr. The glass substrate is moved past these sputtering targets at about 225–500 inches per minute.

In manufacturing float glass, molten glass is floated on a bath of molten tin and the glass is referred to as having an upper side and a lower, or "tin" side. Most commonly, when float glass is provided with a reflective coating, the coating is applied to the upper side of the glass due to some minor surface imperfections in the tin side of the glass which can arise due to contact with support rollers in the annealing lehr. If a sheet of float glass 10 is to be provided with both a water-sheeting coating 20 and a reflective layer 30, it is preferred that the upper surface of the sheet glass be used as the interior surface 14 of the glass to receive the reflective coating 30 while the tin side of the glass is used as the exterior surface to receive the water-sheeting coating 20.

Figure 6:
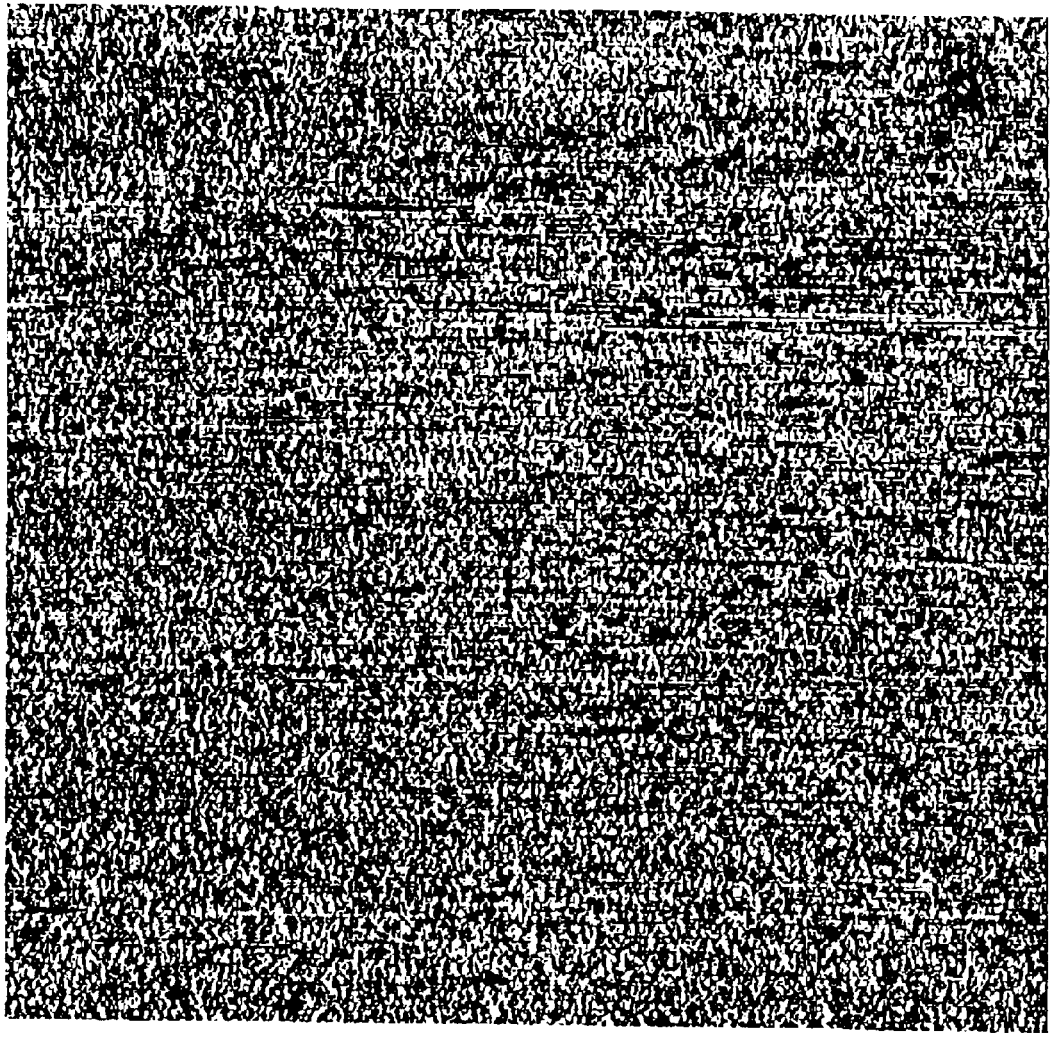
FIG. 6 is an atomic force micrograph of a plain, uncoated surface of a sheet of conventional float glass.
Figure 7:
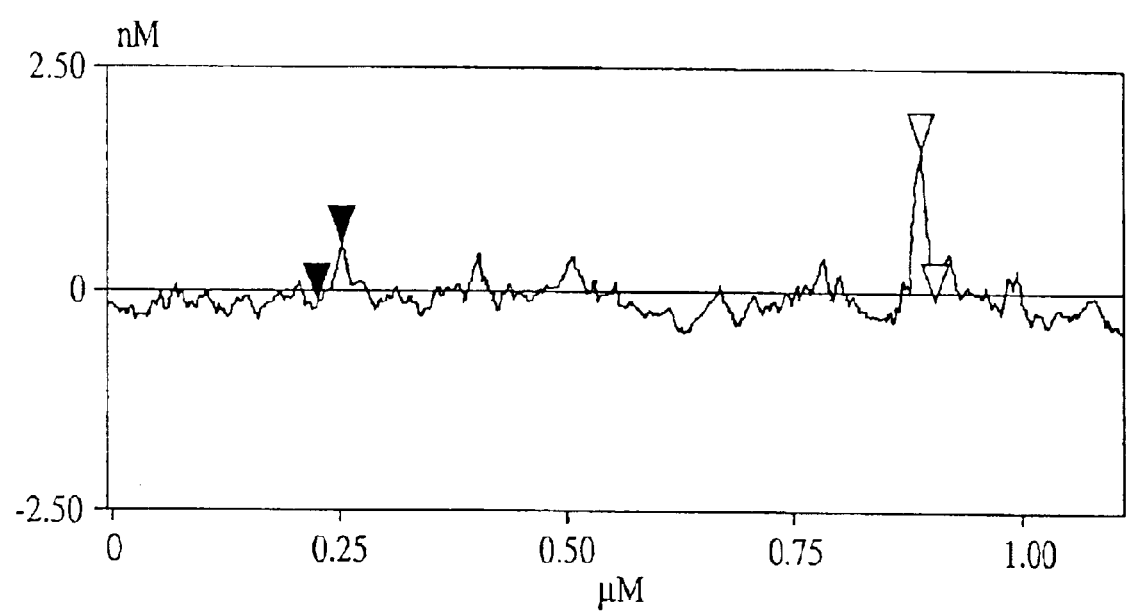
FIG. 7 is a graph showing a height profile across a short length of the surface of the sheet of glass shown in FIG. 6.

FIG. 6 is an atomic force micrograph of one square micron ($\mu$m) of the surface of the tin side of an untreated sheet of float glass. FIG. 7 is a graph representing a profile of the same side of the sheet of glass along about a 1 $\mu$m line on that surface. Both of these images were obtained by atomic force microscopy using a Digital Instruments Nanoscope III using a standard silicon tip.

FIGS. 6 and 7 illustrate a relatively smooth surface. While this surface is not perfectly smooth and it appears to have a slightly rough appearance in FIG. 6, it is important to note that the scale of these images is quite small. To place these images in perspective, two peaks in the profile of FIG. 7 are highlighted by a pair of arrows. The two darker arrows toward the left in FIG. 7 (at about 0.25 $\mu$m along the abscissa) mark the beginning and the apex of a first peak A; the two lighter arrows toward the right in FIG. 7 (at about 0.9 $\mu$m along the abscissa) mark the apex and end of a second peak B. The first peak A is less than 0.7 nm in height while the second, taller peak B is only about 1.7 nm tall.

Figure 8:
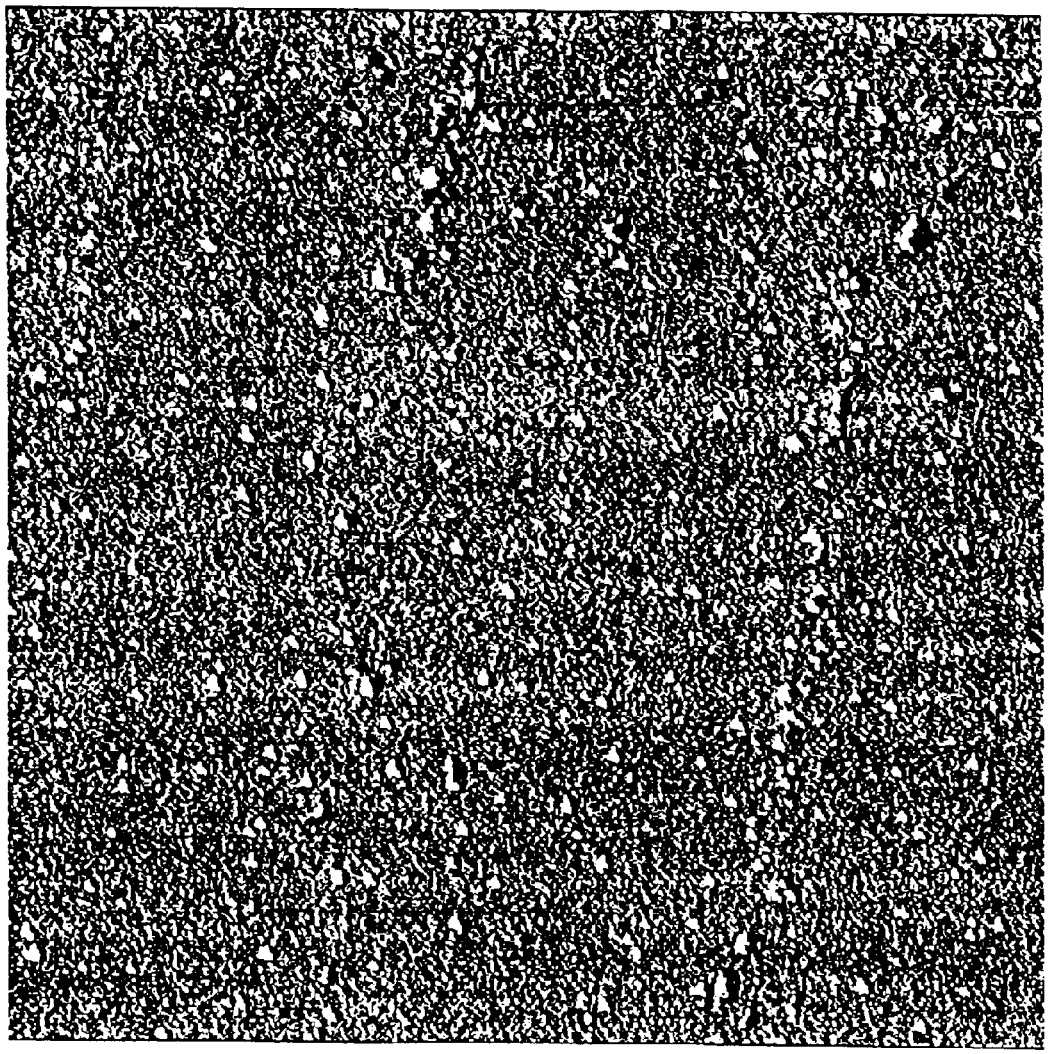
FIG. 8 is a atomic force micrograph of a surface of a sheet of float glass bearing a water-sheeting coating in accordance with the invention.
Figure 9:
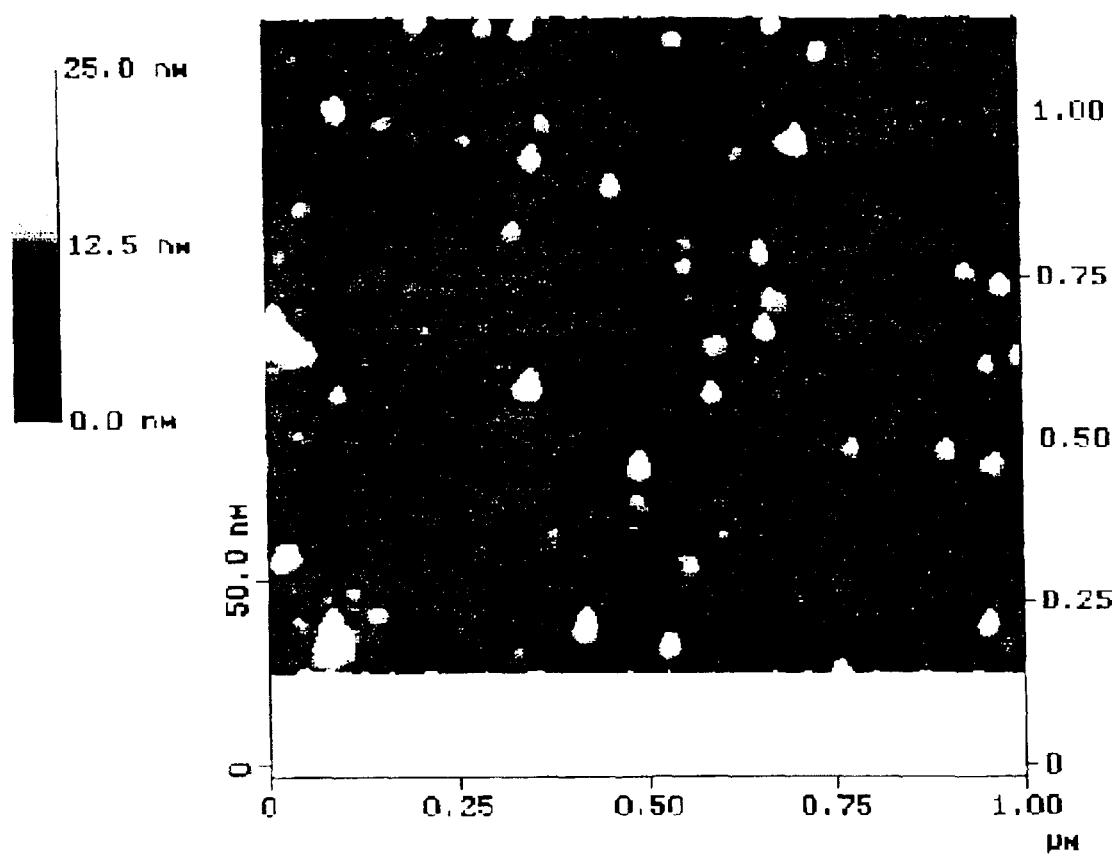
FIG. 9 is a three-dimensional representation of an area of the same sheet of float glass illustrated in FIG. 8.
Figure 10:
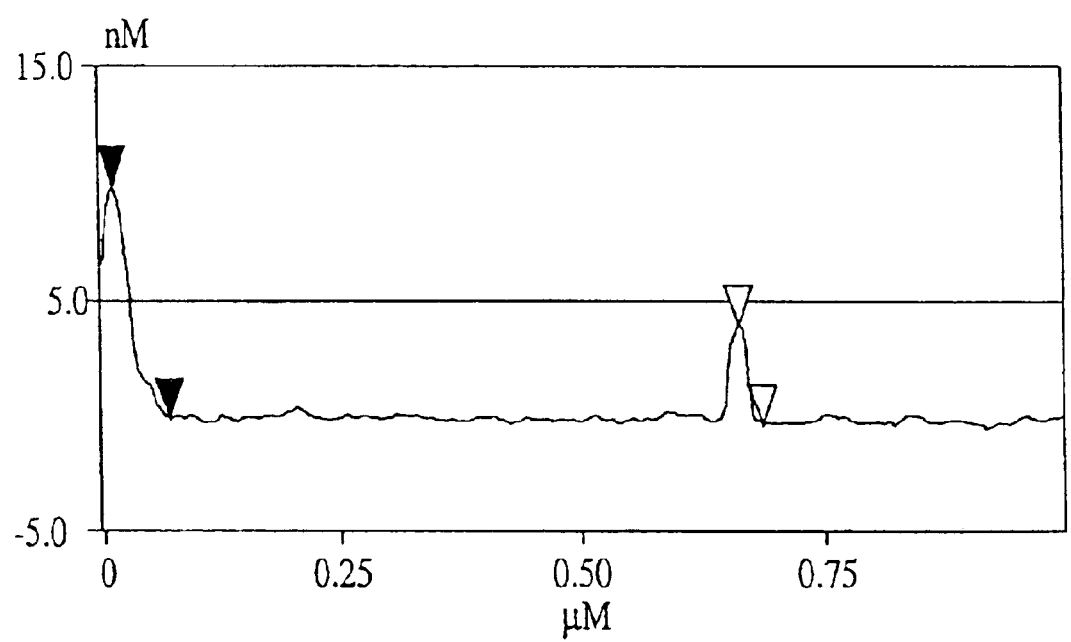
FIG. 10 is a graph similar to FIG. 7, but showing a height profile across a short length of the surface of the water-sheeting coating shown in FIGS. 8 and 9.

FIGS. 8–10 are analogous representations of a sheet of float glass on the tin side of which a water-sheeting coating of the invention has been applied. FIG. 8 is a micrograph much like FIG. 6, also representing 1 $\mu$m$^2$ of the surface. FIG. 10 is a graph much like FIG. 7, but wherein the ordinate axis represents a range of 20 nm rather than the smaller 5 nm range of FIG. 7. FIG. 9 is a perspective view which highlights the surface features of the water-sheeting coating. The smaller vertical bar to the right of the primary image is a legend representing the gray scale associated with different heights from the base surface.

By comparing these two sets of figures, it appears that the water-sheeting coating of the invention has a significantly more irregular surface than does the uncoated surface shown in FIGS. 6 and 7. In FIG. 8, there appear to be a series of spaced-apart projections rising from the surface of the glass, but it is difficult to determine in this view the height of these projections. FIGS. 9 and 10 give a better indication of the height and shapes of these projections. In FIG. 10, the two darker arrows highlight the apex and end of one peak A while the two lighter arrows point to the apex and end of a second peak B. In contrast to the rather small peaks in FIG. 7, the second, smaller peak B in FIG. 10 is about 4.3 nm tall while the first peak A is nearly 10 nm tall. This is over five times as tall as the peaks illustrated in FIG. 7.

It is also worth noting that the surface of the coating shown in FIGS. 8–10 is uneven, but appears to be relatively non-porous. This is in sharp contrast to the photomicrographs in Takamatsu et al.'s U.S. Pat. No. 5,394,269, which show a porous sol gel-derived coating having pores on the order of 50–200 nm penetrating the coating.

For reasons which are not currently understood, these images suggest that sputter depositing silica on the surface of the glass yields a coating with a surface having a series of fairly sharp, distinct peaks. No meaningful statistical analysis of coated surfaces have been performed, so it is not known if FIGS. 6–10 are representative of their respective surfaces. As a matter of fact, it is acknowledged that these images could be a typical of the overall surfaces of the samples in question, so it may not be appropriate to attach too much significance to the apparent differences in the surface structure of these two glasses. However, this data does suggest that the surface of the water-sheeting coating 20 of the invention is relatively non-porous and differs from an untreated float glass surface in that it is significantly more uneven and irregular, having a number of discrete, spaced-apart peaks rising significantly above the rest of the surface.

The behavior of a sheet of glass coated with a water-sheeting coating of the invention is visibly different from that of a similar sheet of glass not bearing the present coating. A glass surface bearing a water-sheeting coating 20 tends to sheet water more readily and is noticeably easier to clean without any visible streaks or defects than is a comparable sheet of glass under the same conditions.

To provide an accurate comparison of a coating of the invention to a directly comparable sheet of glass not bearing the coating, a comparative sample was prepared. A plain, untreated pane of glass was thoroughly cleaned and laid horizontally on a set of rollers. A small, square piece of glass was laid on the upper surface of the pane of glass to serve as a template covering part of the surface of the pane. The pane and overlying template were passed into a magnetron sputtering chamber and a coating of about 35 Å of $SiO_2$ was deposited. The template was then removed, leaving a pane of glass with a water-sheeting coating 20 of the invention over most of its surface, but having an uncoated area which was beneath the template during the sputtering operation. The opposite side of the glass, i.e., the side of the glass facing away from the side provided with the $SiO_2$ coating, was coated with a low emissivity, infrared-reflective film stack having two silver layers spaced apart from one another and from the glass using a plurality of dielectric layers.

The partially coated surface of the glass pane was visibly inspected. When completely clean, the boundaries of the uncoated area which underlied the template during sputtering was essentially undetectable to the unaided eye, indicating that the water-sheeting coating had a minimal impact on the basic optical properties of the glass. A fine spray of atomized water droplets was sprayed on the surface using a simple, hand-operated spray bottle of the type conventionally used to spray household cleaning products. Once the spray was applied, the boundaries of the uncoated area were readily visible. The water on the area bearing the coating 20 sheeted to an apparently uniform film of water, but the area without the coating had a less uniform appearance.

A conventional cleaning solution commercially available under the trademark Windex® was sprayed on the surface of the glass pane and the surface was wiped with a paper towel until the area bearing the coating 20 appeared dry and no longer showed any visible streaks. When wiping ceased, the uncoated area still had visible streaks of moisture. While these visible streaks on the uncoated area eventually dried without leaving any substantial residual streaking on the glass, it is believed that the average person would tend to continue to wipe this area until all visible streaks disappeared, meaning that the person would expend less time and effort cleaning a glass article bearing a water-sheeting coating 20 than a glass article without such a coating.

The change in surface properties brought about by the present invention are readily discernable on a qualitative level, but it can be more difficult to quantify these differences in a meaningful manner. Nonetheless, the following examples are believed to illustrate the difference between an uncoated sheet of glass and a sheet of glass bearing a water-sheeting coating 20 of the invention. In each of the following Experimental Examples 1–3, two test samples, Sample A and Sample B, were provided. Sample A comprised a plain sheet of soda-lime glass and Sample B was a similar sheet of soda-lime glass bearing a water-sheeting coating 20 of the invention. The water sheeting coating was applied using three 95% silicon/5% aluminum rotary targets at a power level of 42 kW in an oxygen atmosphere of about 3.5 mT with the glass moving at a rate of about 500 inches per minute.

EXPERIMENTAL EXAMPLE 1

Both of the samples were subjected to a salt spray test in accordance with ASTM B117 using a 5% salt solution for 250 hours. Briefly, the samples were cleaned and placed in a Singleton SCCH #20 Corrosion Cabinet at an angle of about 15–30° from vertical, with Sample B being oriented such that the surface bearing the water-sheeting coating 20 was oriented to face downwardly. A 5% salt solution (5 wt % sodium chloride, 95 wt % distilled water) was atomized in the cabinet at about 35° C. for 250 hours, with the salt solution being collected at a rate of about 1.8 ml per 80 cm per hour in the collection cylinders in the cabinet. Thereafter, the samples were removed from the cabinet, rinsed, allowed to dry and visually inspected. Sample A had more numerous water spots than did Sample B and the water spots on Sample A were more visible than the light streaks on Sample B.

Each sample was then cleaned using paper towels and Windex®. The haze of each sample was then measured using a BVK-Gardner Haze-Gard Plus according to ASTM D-1003 and ASTM D-1044, employing an integrating sphere integrating light over the spectral range associated with the CIE-C standard. Sample A, the standard glass sheet, had a haze measurement of about 0.15% while the haze measurement on Sample B, the sample bearing a water-sheeting coating 20, was about 0.10%.

The contact angle of the water on the surface of the glass sheet was then measured using a commercially available measuring device, with the contact angle for Sample B being measured on the surface bearing the coating 20. The contact angle for Sample A was about 32 degrees; the contact angle for Sample B was about 12 degrees.

EXPERIMENTAL EXAMPLE 2

Handling the samples with tongs, each sample was first dipped in a beaker of boiling tap water maintained at about 100° C. and held there for about 5 seconds, after which it was deposited in a beaker of ice water maintained at about 0° C. and held there for about 5 seconds. This process was repeated 25 times. The samples were then placed in a Singleton Model SL23 humidity test chamber maintained at about 90% relative humidity at about 120° F. (about 49° C.) for about 500 hours. Each sample was then visually inspected. As in Experimental Example 1, it was determined that Sample A exhibited more numerous and more visible water spots than did Sample B.

Each sample was then cleaned and the haze and contact angle measurements were taken in much the same manner outlined above in Experimental Example 1. The haze measurement for Sample A was 0.34% while that for Sample B was 0.14%. Sample A exhibited a contact angle of about 20° while the contact angle for Sample B was about 12°.

EXPERIMENTAL EXAMPLE 3

Two samples of uncoated glass (Samples A1 and A2) and two samples of coated glass (Samples B1 and B2) were cleaned and their haze measurements were taken. Each of the uncoated samples had haze measurements of about 0.09% while the haze measurement for the glass with a water-sheeting coating 20 was about 0.08%.

A cement mixture was prepared by mixing 4 ounces (about 11.5 g) of portland cement to 1000 ml of water. Two samples of uncoated glass (Samples A1 and A2) and two samples of coated glass (Samples B1 and B2) were held in this solution for about ten minutes then removed. Samples A1 and B1 were then rinsed liberally with water (but without any rubbing) and allowed to dry; Samples A2 and B2 were allowed to air dry without rinsing.

All four samples were hand cleaned using Windex® and paper towels. The residual soiling on Samples A1 and A2 from the cement test smeared during this cleaning, making it more difficult to clean the glass. In contrast, neither Samples B1 not Sample B2 smeared and both of these samples dried noticeably quicker than Sample A1 or Sample A2, respectively.

Once the samples had been thoroughly hand cleaned, haze and contact angle measurements were made. After the cement treatment, the haze for Samples A1 and B1 remained unchanged at 0.09% and 0.08%, respectively. The haze measurement for Sample B2 likewise remained unchanged at about 0.08%, but the haze measurement for Sample A2 increased slightly from about 0.09% to about 0.10%. The contact angle for Samples A1 and A2 were measured prior to the cement treatment at about 26°; Samples B1 and B2 had contact angles of about 11° at the same stage. After the cement treatment, the contact angle for Sample A1 was about 32° while the contact angle for Sample B1, the other rinsed sample, was about 100°. The contact angle for Sample A2 was about 33° while the contact angle for Sample B2, the other air-dried sample, was about 14°.

EXPERIMENTAL EXAMPLE 4

The performance of glass bearing a water-sheeting coating 20 of the invention was compared to plain, uncoated glass and to other glass coatings which claim to make the surface easier to clean. Each sample started with a sheet of float glass and, aside from the uncoated glass sample, had a coating applied to a surface thereof; the sample ID assigned to each sample type and the coating applied thereto is set forth in the following table:

| Sample ID | Coating applied |
|---|---|
| 168 | 35 Å $SiO_2$ sputtered using 100% $O_2$ |
| 169 | 50 Å $SiO_2$ sputtered using 100% $O_2$ |
| 170 | 50 Å $SiO_2$ sputtered using 80/20 mixture of $O_2$/Ar |
| 171 | 100 Å $SiO_2$ sputtered using 80/20 mixture of $O_2$/Ar |
| 173 | Window Maid ™ coating, commercially available from _____, applied in accordance with manufacturer's instructions |
| 174 | Glass Shield ™ coating, commercially available from _____, applied in accordance with manufacturer's instructions |
| 175 | Clear Shield ™ coating, commercially available from _____, applied in accordance with manufacturer's instructions |
| 176 | uncoated glass |

A set of these samples were subjected to an accelerated weathering test and the contact angle and ease of cleaning was checked on a periodic basis. In the weathering test, samples were placed in a stainless steel enclosure maintained at a temperature of about 160° F. (about 71° C.). A 300W ultraviolet light source (sold by Osram under the trade name Ultra-Vitalux) was positioned toward the bottom of the enclosure and samples were positioned at an angle of about 45° with respect to horizontal with the bottom edges of the sample spaced about 10 inches (about 25 cm) from the bulb. Periodically, the samples were removed from the enclosure and the contact angle was measured in much the same manner as that outlined above. The contact angles were as follows:

| | Contact Angle, by number of days in weathering test | | | | | | |
|---|---|---|---|---|---|---|---|
| Sample ID | 0 | 1 | 2 | 3 | 4 | 5 | 10 |
| 168 | 13 | | | 20 | | | |
| 169 | 11 | 14.3 | 17.7 | 21 | 27 | 33 | |
| 170 | 11 | | | 17 | 25.5 | 34 | |
| 171 | 6 | 26.5 | 26.5 | 32 | 33 | 34 | |
| 173 | 41 | | | 50 | 51.5 | 53 | 42 |
| 174 | 23 | | | 48 | 48.5 | 49 | 46 |
| 175 | 74 | | | 62 | 66 | 70 | 66 |
| 176 | 35 | 35 | | | | 31 | 35 |

In addition, the ease of cleaning the sample was tested by spraying Windex® on the coated surface of the sample or, in the case of the uncoated sample, on the surface which was in contact with the tin bath during the float manufacturing process. That surface was manually wiped with a paper towel until the surface appeared to be clean and essentially streak-free. The ease of cleaning was determined on scale of 1–5, with the ease of cleaning normal, uncoated glass prior to any environmental exposure being defined as 3, a very easy to clean glass surface being rated 1 and a sample which is substantially more difficult to clean being rated 5. (While this rating system is somewhat subjective, it does give a rough qualitative indication of the ease with which the glass can be cleaned.) The results of this testing were as follows:

| | Contact Angle, by number of days in weathering test | | | | | | |
|---|---|---|---|---|---|---|---|
| Sample ID | 0 | 1 | 2 | 3 | 4 | 5 | 10 |
| 168 | 1 | 1.5 | 1.5 | 2 | 3 | | |
| 169 | 1 | 1.5 | 1.5 | 2 | 3 | 4 | |
| 170 | 1 | 1 | 1 | 1.5 | 3 | 4 | |
| 171 | 1 | 3 | 3 | 3 | 3 | 4 | |
| 173 | 4 | 4 | 4 | 5 | 5 | 4 | 4 |
| 174 | 5 | 5 | 5 | 5 | 5 | 5 | 5 |
| 175 | 5 | 5 | 5 | 5 | 5 | 5 | 5 |
| 176 | 3 | 3 | | | | | 3 |

These results indicate that a water-sheeting coating 20 of the invention makes the glass surface significantly easier to clean than either the standard, uncoated glass or glass coated with any one of several commercially available coatings designed to make glass easier to clean. As a matter of fact, these commercially available coatings actually made the glass seem more difficult to clean. (While these coatings may be effective in some applications, it is believed that the "ease of cleaning" standards employed in this Experimental Example are fairly representative of how an average home owner would perceive ease of cleaning. For example, even if streaks of the cleaning fluid on the pane of glass might dry without leaving any permanent streaks, an average person is likely to keep wiping the area until the glass appears clean to avoid any residual streaking.)

The advantageous effects of the water-sheeting coating of the invention did appear to drop off over time in this accelerated weathering test. In particular, after 5 days or so in this test, coatings of the invention yielded results comparable to those achieved with uncoated glass samples. Even after such degradation, the samples bearing a water-sheeting coating 20 had a lower contact angle and remained easier to clean than did the commercially available coatings evaluated in these tests.

It is unclear what correlation there may be between time of ordinary exposure to the elements and time in the accelerated weathering test used in this example. It is believed, however, that a coating 20 of the invention will continue to show enhanced cleanability for an extended period of time. As a matter of fact, preliminary tests indicate that much of the benefit of the coating 20 may be restored with appropriate cleaning even after degradation in accelerated weathering testing, suggesting that the benefits of the coating can be restored relatively simply even after they have diminished due to exposure to the elements.

While a preferred embodiment of the present invention has been described, it should be understood that various changes, adaptations and modifications may be made therein without departing from the spirit of the invention and the scope of the appended claims.

What is claimed is:

1. A method of rendering surfaces of a pane of glass resistant to soiling and staining, comprising:
    a) providing a sheet of glass having a clean interior surface and a clean exterior surface;
    b) sputtering silica directly onto the interior surface of the sheet of glass, thereby yielding a first water-sheeting coating having a contact angle with water below about 25° which causes water applied to said interior surface to sheet; and
    c) sputtering silica directly onto the exterior surface of the sheet of glass, thereby yielding a second water-sheeting coating having a contact angle with water below about 25° which causes water applied to said exterior surface to sheet.

2. The method of claim 1 further comprising exposing one of the interior and exterior surfaces of the sheet of glass to periodic contact with water, the water-sheeting coating on the exposed surface reducing soiling and staining that would otherwise result from the periodic contact with water.

3. The method of claim 1 wherein the first and second water-sheeting coatings are sputtered from a silicon target in an oxygen-containing sputtering chamber.

4. A method of coating two sides of a pane of glass in a single pass through a coating apparatus, comprising:
    a) providing a sheet of glass having a clean first surface and a clean second surface;
    b) providing a sputtering chamber having a plurality of rollers that define a substrate support therein, the chamber having an upper target positioned above the support and being adapted to downwardly sputter, the chamber having a lower target positioned below the support and being adapted to upwardly sputter;
    c) positioning the sheet of glass in the chamber such that the first surface of the sheet of glass rests on one or more of the rollers and is oriented toward the lower target, whereby the second surface of the sheet of glass is oriented toward the upper target;
    d) sputtering the lower target to deposit a first water-sheeting coating on the first surface of the glass, the first water-sheeting coating having a contact angle with water below about 25° which causes water applied to said first surface to sheet; and
    e) sputtering the upper target to deposit a second water-sheeting coating on the second surface of the glass, the second water-sheeting coating having a contact angle with water below about 25° which causes water applied to said second surface to sheet.

5. The method of claim 4 wherein the upper and lower targets are sputtered substantially simultaneously.

6. The method of claim 4 wherein the upper and lower targets comprise silicon and are sputtered in an oxidizing atmosphere.

7. The method of claim 4 wherein the first and second water-sheeting coatings each has a median thickness of between about 15 angstroms and about 350 angstroms.

8. The method of claim 7 wherein the median thickness is between about 15 angstroms and about 150 angstroms.

9. The method of claim 8, wherein the median thickness is between about 20 angstroms and about 120 angstroms.

10. The method of claim 4 wherein the first and second water-sheeting coatings each is an exposed, outermost coating on the glass sheet.

11. A method of rendering a glass surface resistant to soiling and staining, comprising:
    a) providing a sheet of glass having a clean interior surface and a clean exterior surface;
    b) providing a sputtering line comprising a series of sputtering chambers, each sputtering chamber having a plurality of rollers that define a substrate support, the sputtering line having an upward sputtering chamber with a lower target positioned below the rollers in that chamber;
    c) positioning the sheet of glass in the upward sputtering chamber such that the exterior surface of the sheet of glass rests on two or more of the rollers in that chamber; and
    d) sputtering the lower target to deposit silica directly onto the exterior surface of the glass, thereby yielding a water-sheeting coating having a contact angle with water below about 25° which causes water applied to the exterior surface to sheet, the sputtered silica traveling between said two or more rollers before being deposited on the exterior surface of the sheet of glass.

12. The method of claim 11 wherein the lower target comprises silicon and is sputtered in an oxidizing atmosphere.

13. The method of claim 11 wherein the upward sputtering chamber is a last of the sputtering chambers in the sputtering line.

14. The method of claim 11 further comprising providing a downward sputtering chamber having an upper sputtering target and sputtering the upper target to deposit a low emissivity coating onto the interior surface of the glass sheet.

15. The method of claim 11 wherein the water-sheeting coating has a median thickness of between about 15 angstroms and about 350 angstroms.

16. The method of claim 15 wherein the median thickness is between about 15 angstroms and about 150 angstroms.

17. The method of claim 16 wherein the median thickness is between about 20 angstroms and about 120 angstroms.

18. The method of claim 11 wherein the water-sheeting coating is an exposed, outermost coating on the glass sheet.

* * * * *